US011161807B2

(12) United States Patent
Ayzac et al.

(10) Patent No.: US 11,161,807 B2
(45) Date of Patent: Nov. 2, 2021

(54) THERMO-THICKENING COMPOUNDS FOR NON-POLAR LIQUID

(71) Applicants: SORBONNE UNIVERSITE, Paris (FR); CENTRE NATIONAL DE LA RECHERCHE SCIENTIFIQUE, Paris (FR)

(72) Inventors: Virgile Ayzac, Paris (FR); Laurent Bouteiller, Bourg-la-Reine (FR); Matthieu Raynal, Carrières-sur-Seine (FR); Benjamin Isare, Frévillers (FR)

(73) Assignees: SORBONNE UNIVERSITE, Paris (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days.

(21) Appl. No.: 16/468,427

(22) PCT Filed: Dec. 12, 2017

(86) PCT No.: PCT/EP2017/082431
§ 371 (c)(1),
(2) Date: Jun. 11, 2019

(87) PCT Pub. No.: WO2018/108916
PCT Pub. Date: Jun. 21, 2018

(65) Prior Publication Data

US 2020/0010410 A1 Jan. 9, 2020

(30) Foreign Application Priority Data

Dec. 12, 2016 (EP) .................................... 16203527

(51) Int. Cl.
*C07C 275/42* (2006.01)
*C07C 227/12* (2006.01)
(Continued)

(52) U.S. Cl.
CPC .......... *C07C 275/42* (2013.01); *C07C 227/12* (2013.01); *C07C 273/1809* (2013.01);
(Continued)

(58) Field of Classification Search
CPC ................ C07C 275/42; C07C 227/12; C07C 273/1809; C07C 381/12; C10N 2050/10;
(Continued)

(56) References Cited

U.S. PATENT DOCUMENTS

2007/0160635 A1* 7/2007 Chodorowski-Kimmes ................ A61K 8/37 424/401
2009/0163595 A1* 6/2009 Yang ....................... A61P 25/08 514/616

FOREIGN PATENT DOCUMENTS

WO 2014/096323 A1 6/2014

OTHER PUBLICATIONS

Ayzac, V., Raynal, M., Isare, B., Ide, J., Brocorens, P., Lazzaroni, R., Etienne, T., Monari, A., Assfeld, X., Bouteiller, L., "Probing halogen-halogen interactions in solution", Phys. Chem. Chem. Phys., 2017, 19, 32443-32450 (Year: 2017).*

(Continued)

*Primary Examiner* — James C Goloboy
(74) *Attorney, Agent, or Firm* — Maier & Maier, PLLC

(57) ABSTRACT

A bis-urea compound of general formula (IV):

(IV)

(Continued)

The compound is useful as a thermo-thickening agent in a non-polar liquid such as engine lubricating oil or thermo-setting varnish. Also, a method for preparing the thermo-thickening compound. Further, a composition comprising the thermo-thickening compound and a non-polar liquid.

16 Claims, 3 Drawing Sheets

(51) Int. Cl.

| | |
|---|---|
| ***C07C 273/18*** | (2006.01) |
| ***C07C 381/12*** | (2006.01) |
| ***C10L 1/222*** | (2006.01) |
| ***C10L 10/14*** | (2006.01) |
| ***C10M 115/08*** | (2006.01) |
| ***C10N 30/02*** | (2006.01) |
| ***C10N 50/10*** | (2006.01) |
| ***C10M 133/20*** | (2006.01) |

(52) U.S. Cl.

CPC .......... *C07C 381/12* (2013.01); *C10L 1/2227* (2013.01); *C10L 10/14* (2013.01); *C10M 115/08* (2013.01); *C10M 133/20* (2013.01); *C10M 2215/1026* (2013.01); *C10N 2030/02* (2013.01); *C10N 2050/10* (2013.01)

(58) Field of Classification Search

CPC ... C10N 2030/02; C10L 1/2227; C10L 10/14; C10M 115/08; C10M 133/20; C10M 2215/1026

See application file for complete search history.

(56) References Cited

OTHER PUBLICATIONS

Dirany, M., Ayzac, V., Isare, B., Raynal, M., Boutellier, L. "Structural control of bisurea-based supramolecular polymers: influence of an ester moiety—Supporting Information", Langmuir, 2015 (Year: 2015).*

International Search Report and Written Opinion of the International Searching Authority dated Jun. 3, 2018 in corresponding International application No. PCT/EP2017/082431; 11 pages.

Lortie et al., "Structural and Rheological Study of a Bis-urea Based Reversible Polymer in an Apolar Solvent", Langmuir, 2002, p. 7218-7222, vol. 18, No. 19; 6 pages.

Haridas et al., "1,3-Phenyl linked urea-based receptors for anions and the facile cyclization to imidazolidinedione", Tetrahedron Letters, 2012, p. 5523-5527, vol. 53, No. 41; 6 pages.

Zhang et al., "Comparative Analysis of Pharmacophore Features and Quantitative Structure-Activity Relationships for CD38 Covalent and Non-covalent Inhibitors", Chemical Abstracts Service, Database CA [Online], retrieved on Sep. 26, 2017; 2 pages.

Dirany et al., "Structural Control of Bisurea-Based Supramolecular Polymers: Influence of an Ester Moiety", Langmuir, 2015, p. 11443-11451, vol. 31, No. 42; 10 pages.

Dirany et al., "Structural Control of Bisurea-Based Supramolecular Polymers: Influence of an Ester Moiety—Supporting information", Langmuir, 2015, URL:http://pubs.acs.org/toc/langd5/31/42, retrieved on Sep. 26, 2017; 24 pages.

Beckman et al., "Generation of Microcellular Materials via Self-Assembly in Carbon Dioxide", Chem. Mater, 2002, p. 4273-4280, vol. 14, No. 10; 8 pages.

* cited by examiner

THERMO-THICKENING COMPOUNDS FOR NON-POLAR LIQUID

FIELD OF INVENTION

The present invention relates to the field of thermo-thickeners. More precisely, the invention relates to bis-urea compounds useful as a thermo-thickening agents in non-polar liquids, such as for example engine lubricating oils or thermosetting resins. The present invention also concerns a method for preparing said thermo-thickening compounds. The present invention also relates to compositions comprising said thermo-thickening compounds.

BACKGROUND OF INVENTION

As a general rule, the viscosity of a fluid decreases when temperature increases. However, for some applications, being able to avoid such decrease of viscosity is essential. Thus, using additives able to compensate this effect is necessary in such cases. In aqueous medium, numerous solutions exist. However, this is not the case in organic medium.

For example, in the engine lubricating field, an efficient lubricating oil has to avoid (i) metal engine surfaces rubbing together and wear out, and (ii) the agglomeration of deposits by maintaining them in suspension. If the viscosity is too high at low temperatures, the oil cannot flow into the engine. Besides, if the viscosity is too low when the engine is hot, the oil cannot ensure efficient mechanical properties and may disrupt the engine operation.

Therefore, one of the essential requirement for a lubricating oil is that at low temperatures, it has a low viscosity to assist in cold starting, while at higher temperatures, its viscosity should be maintained for keeping efficient mechanical properties.

Today, very few suitable solutions are available in the market for allowing enhancing the rheological properties of non-polar media (such as fuel, engine lubricating oil, etc . . . ) having constraints as those mentioned above.

Thus, there is a need for providing thermo-thickening agents suitable for non-polar liquids. By “thermo-thickening” it is herein referred to the ability to counteract the natural decrease of viscosity of a liquid upon temperature rise.

Surprisingly, the Applicant herein evidences that bis-urea compounds may be used as efficient thermo-thickening agents.

Bis-urea have already been disclosed for various applications; in particular as organogelling agent. For instance, WO2014/096323 discloses the use of bis-urea compounds for providing gelled hydrocarbon-based fuel composition at room temperature. In WO2014/096323, the viscosity of the gelled fuel decreases when a shear stress is applied to said gel. WO2014/096323 does not disclose nor suggest that bis-urea compounds disclosed therein may be able to maintain or increase the viscosity of a non-polar solution, upon heating.

Advantageously, the compounds of the invention are easily solubilized in a liquid; especially, in a non-polar liquid. Advantageously, the compounds of the invention do not lead to deposits. Advantageously, the compounds of the invention are easily tunable. Advantageously, the compounds of the invention are enantiopure compounds.

SUMMARY

This invention thus relates to the use as thermo-thickening agent of a compound of general formula (IV):

(IV)

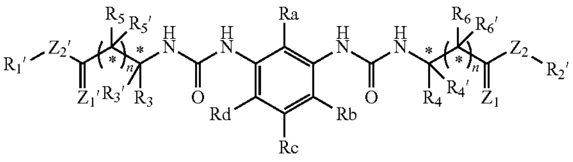

wherein:

$R_a$, $R_b$, $R_c$ and $R_d$ are each independently selected from H, alkyl, heteroalkyl, alkoxy, amino, alkylamino and halo; preferably $R_b$ and $R_d$ are each independently selected from H, $C_1$-$C_4$ alkyl, $C_1$-$C_4$ heteroalkyl, $C_1$-$C_4$ alkoxy, $C_1$-$C_4$ dialkylamino and halo; more preferably $R_b$ and $R_d$ are each independently selected from at least one $C_1$-$C_4$ alkyl or halo;

$R_1$' and $R_2$' are each independently selected from linear alkyl, heteroalkyl, alkenyl, heteroalkenyl, alkynyl, heteroalkynyl and macromolecular groups, optionally substituted by one or more halo; preferably $R_1$' and $R_2$' are each independently selected from linear alkyl or linear heteroalkyl group, said linear group being optionally substituted by one or more halo; more preferably $R_1$' and $R_2$' are each independently selected from linear $C_6$-$C_{18}$ alkyl or heteroalkyl group, said linear group being optionally substituted by one or more terminal halo;

$R_3$', $R_3$, $R_4$, $R_4$' $R_5$', $R_5$, $R_6$ and $R_6$' are each independently selected from H, alkyl, alkenyl, aryl, heteroalkyl, heteroalkenyl, heteroaryl, alkylaryl, arylalkyl, heteroarylalkyl or alkylheteroaryl, optionally substituted by guanidine, aryl, pyrrolidine, imidazole, hydroxyaryl, carboxy, selanyl, hydroxyl, amide, thiol, alkylthio, amino, deuterium or halo; preferably $R_3$', $R_3$, $R_4$, $R_4$' $R_5$', $R_5$, $R_6$ and $R_6$' are each independently selected from H, $C_1$-$C_{12}$ alkyl substituted by at least one aryl, said aryl being optionally substituted by one or more halo or deuterium;

$Z_1$ and $Z_1$' are each independently selected from O and S atoms;

$Z_2$ and $Z_2$' are each independently selected from —NH—, O and S atoms;

n represents a positive integer from 0 to 10; preferably n is equal to 0; and optionally, * stands for a stereogenic center;

provided that $R_1$' and $R_2$' does not represent both a methyl group.

According to one embodiment, the compound is of general formula (IV bis):

(IVbis)

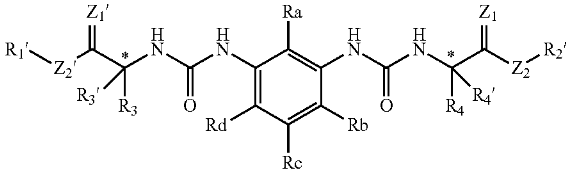

wherein $R_a$, $R_b$, $R_c$, $R_d$, $R_1$', $R_2$', $R_3$, $R_3$', $R_4$, $R_4$', $Z_1$, $Z_1$', $Z_2$ and $Z_2$' are as defined in formula (IV).

According to one embodiment, the compound of formula (IVbis), $R_a$ and $R_c$ are both H.

According to one embodiment, the thermo-thickening agent is used for a non-polar liquid; preferably the non-polar liquid is selected from an oil, a grease, a monomer, a thermosetting resin, a perfume or a fuel.

According to one embodiment, the thermo-thickening is performed at a temperature ranging from 5° C. to 100° C.; preferably from 10° C. to 60° C.; more preferably from 20° C. to 50° C.

According to one embodiment, the invention refers to the use as thermo-thickening agent of a compound of general formula (IV) for further improving the cold flow property of a non-polar liquid.

The present invention also refers to a compound of general formula (IV):

(IV)

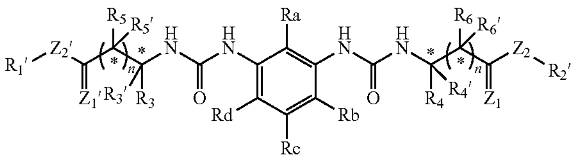

wherein:

$R_a$, $R_b$, $R_c$ and $R_d$ are each independently selected from H, alkyl, heteroalkyl, alkoxy, amino, alkylamino and halo; preferably $R_b$ and $R_d$ are each independently selected from H, $C_1$-$C_4$ alkyl, $C_1$-$C_4$ heteroalkyl, $C_1$-$C_4$ alkoxy, $C_1$-$C_4$ dialkylamino and halo; more preferably $R_b$ and $R_d$ are each independently selected from at least one $C_1$-$C_4$ alkyl or halo;

$R_1$' and $R_2$' are each independently selected from linear alkyl, heteroalkyl, alkenyl, heteroalkenyl, alkynyl, heteroalkynyl and macromolecular groups, optionally substituted by one or more halo; preferably $R_1$' and $R_2$' are each independently selected from linear alkyl or linear heteroalkyl group, said linear group being optionally substituted by one or more halo; more preferably $R_1$' and $R_2$' are each independently selected from linear $C_6$-$C_{18}$ alkyl or heteroalkyl group, said linear group being optionally substituted by one or more terminal halo;

$R_3$', $R_3$, $R_4$, $R_4$' $R_5$', $R_5$, $R_6$ and $R_6$' are each independently selected from H, alkyl, alkenyl, aryl, heteroalkyl, heteroalkenyl, heteroaryl, alkylaryl, arylalkyl, heteroarylalkyl or alkylheteroaryl, optionally substituted by guanidine, aryl, pyrrolidine, imidazole, hydroxyaryl, carboxy, selanyl, hydroxyl, amide, thiol, alkylthio, amino, deuterium or halo; preferably $R_3$', $R_3$, $R_4$, $R_4$' $R_5$', $R_5$, $R_6$ and $R_6$' are each independently selected from H, $C_1$-$C_{12}$ alkyl substituted by at least one aryl, said aryl being optionally substituted by one or more halo or deuterium;

$Z_1$ and $Z_1$' are each independently selected from O and S atoms;

$Z_2$ and $Z_2$' are each independently selected from —NH—, O and S atoms;

n represents a positive integer from 0 to 10; preferably n is equal to 0; and optionally, * stands for a stereogenic center;

provided that $R_1$' and $R_2$' does not represent both a methyl group.

According to one embodiment, n is equal to 0 (i.e. compounds having formula (IV bis)).

According to one embodiment, $Z_1$, $Z_1$', $Z_2$ and $Z_2$' represent O atoms.

According to one embodiment, the compound is selected from:

(2S,2'S)-dihexyl 2,2'-((((4-methyl-1,3-phenylene)bis(azanediyl))bis(carbonyl))bis(azanediyl))bis(3-phenylpropanoate);

(2S,2'S)-diheptyl 2,2'-((((4-methyl-1,3-phenylene)bis(azanediyl))bis(carbonyl))bis(azanediyl))bis(3-phenylpropanoate);

(2S,2'S)-dioctyl 2,2'-((((4-methyl-1,3-phenylene)bis(azanediyl))bis(carbonyl))bis(azanediyl))bis(3-phenylpropanoate);

(2S,2'S)-dioctyl 2,2'-((((4,6-dimethyl-1,3-phenylene)bis(azanediyl))bis(carbonyl))bis(azanediyl))bis(3-phenylpropanoate);

(2S,2'S)-dioctyl 2,2'-((((4,6-dichloro-1,3-phenylene)bis(azanediyl))bis(carbonyl))bis(azanediyl))bis(3-phenylpropanoate);

(2S,2'S)-dinonyl 2,2'-((((4-methyl-1,3-phenylene)bis(azanediyl))bis(carbonyl))bis(azanediyl))bis(3-phenylpropanoate);

(2S,2'S)-dinonyl 2,2'-((((4,6-dimethyl-1,3-phenylene)bis(azanediyl))bis(carbonyl))bis(azanediyl))bis(3-phenylpropanoate);

(2S,2'S)-didecyl 2,2'-((((4-methyl-1,3-phenylene)bis(azanediyl))bis(carbonyl))bis(azanediyl))bis(3-phenylpropanoate);

(2S,2'S)-diundecyl 2,2'-((((4-methyl-1,3-phenylene)bis(azanediyl))bis(carbonyl))bis(azanediyl))bis(3-phenylpropanoate);

(2S,2'S)-didodecyl 2,2'-((((4-methyl-1,3-phenylene)bis(azanediyl))bis(carbonyl))bis(azanediyl))bis(3-phenylpropanoate);

(2S,2'S)-didodecyl 2,2'-((((4,6-dimethyl-1,3-phenylene)bis(azanediyl))bis(carbonyl))bis(azanediyl))bis(3-phenylpropanoate);

(2S,2'S)-ditridecyl 2,2'-((((4-methyl-1,3-phenylene)bis(azanediyl))bis(carbonyl))bis(azanediyl))bis(3-phenylpropanoate);

(2S,2'S)-ditetradecyl 2,2'-((((4-methyl-1,3-phenylene)bis(azanediyl))bis(carbonyl))bis(azanediyl))bis(3-phenylpropanoate);

(2S,2'S)-dihexadecyl 2,2'-((((4-methyl-1,3-phenylene)bis(azanediyl))bis(carbonyl))bis(azanediyl))bis(3-phenylpropanoate);

(2S,2'S)-dihexadecyl 2,2'-((((4,6-dimethyl-1,3-phenylene)bis(azanediyl))bis(carbonyl))bis(azanediyl))bis(3-phenylpropanoate);

(2S,2'S)-dioctadecyl 2,2'-((((4-methyl-1,3-phenylene)bis(azanediyl))bis(carbonyl))bis(azanediyl))bis(3-phenylpropanoate);

(2S,2'S)-dioctyl 2,2'-((((4-methyl-1,3-phenylene)bis(azanediyl))bis(carbonyl))bis(azanediyl))bis(3-pentadeuteriumphenylpropanoate);

(2S,2'S)-bis(12,12,12-tribromododecyl) 2,2'-((((4-methyl-1,3-phenylene)bis(azanediyl))bis(carbonyl))bis(azanediyl))bis(3-phenylpropanoate);

(2S,2'S)-bis(12,12,12-tribromododecyl) 2,2'-((((4,6-dimethyl-1,3-phenylene)bis(azanediyl))bis(carbonyl))bis(azanediyl))bis(3-phenylpropanoate);

(2S,2'S)-bis(12,12,12-tribromododecyl) 2,2'-((((4,6-dichloro-1,3-phenylene)bis(azanediyl))bis(carbonyl))bis(azanediyl))bis(3-phenylpropanoate); and (2S,2'S)-bis(12,12,12-trichlorododecyl) 2,2'-((((4,6-dimethyl-1,3-phenylene)bis(azanediyl))bis(carbonyl))bis(azanediyl))bis(3-phenylpropanoate).

The present invention also refers to a composition comprising at least one compound of the invention, and a non-polar liquid.

According to one embodiment, the liquid is selected from an oil (or lubricant), a grease, a monomer, a thermosetting resin, a perfume or a fuel.

According to one embodiment, the compound is at a concentration ranging from more than 0 to 5% by weight to the total weight of the composition; preferably from 0.1 to 1% by weight to the total weight of the composition.

The present invention also refers to a process for manufacturing a compound of formula (IV bis), comprising reacting at least one ester ammonium salt of formula (A-1):

(A-1)

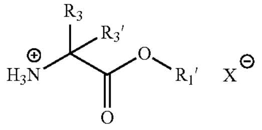

wherein $R_3$' and $R_3$ are each independently selected from H, alkyl, alkenyl, aryl, heteroalkyl, heteroalkenyl, heteroaryl, alkylaryl, arylalkyl, heteroarylalkyl or alkylheteroaryl, optionally substituted by guanidine, aryl, pyrrolidine, imidazole, hydroxyaryl, carboxy, selanyl, hydroxyl, amide, thiol, alkylthio, amino, deuterium or halo;

$R_1$' is each independently selected from linear alkyl, heteroalkyl, alkenyl, heteroalkenyl, alkynyl and heteroalkynyl group, optionally substituted by one or more halo; and $X^-$ is an anion, preferably selected from chloride, bromide, sulfate, hydrogenosulfate and sulfonate; more preferably $X^-$ is tosylate.

with (a) either a diisocyanate of general formula (A-2bis):

(A-2bis)

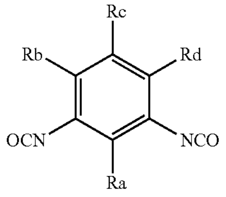

wherein $R_a$, $R_b$, $R_c$ and $R_d$ are each independently selected from H, alkyl, heteroalkyl, alkoxy, amino, alkylamino and halo; preferably $R_b$ and $R_d$ are each independently selected from H, $C_1$-$C_4$ alkyl, $C_1$-$C_4$ heteroalkyl, $C_1$-$C_4$ alkoxy, $C_1$-$C_4$ dialkylamino and halo; more preferably $R_b$ and $R_d$ are each independently selected from at least one $C_1$-$C_4$ alkyl or halo;

(b) or a mixture of reagents allowing the in situ preparation of diisocyanate of formula (A-2bis), preferably a mixture of a compound having a carbonyl function such as bis(trichloromethyl)carbonate or phosgene, and a diamine of formula (A-3bis):

(A-3bis)

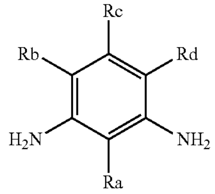

wherein $R_a$, $R_b$, $R_c$ and $R_d$ are defined above.

According to one embodiment, the process of the invention further comprises a preliminary step of preparing ester ammonium salt of formula (A-1) by reacting an amino acid and an alcohol such as hydroxyalkane.

DEFINITIONS

In the present invention, the following terms have the following meanings:

"Thermo-thickening agent": refers to any chemical compound able, when added into a liquid (1) to increase the viscosity of said liquid at room temperature compared to the viscosity of said liquid free of any thermo-thickening agent; and (2) to avoid that, upon temperature rise, the viscosity of said liquid decreases to the same extend than it decreases in absence of any thermo-thickening agent. In a preferred embodiment, as illustrated on FIG. 1, if in absence of the thermo-thickening agent the viscosity of a liquid decreases of x, from $\mu_{liq-1}$ to $\mu_{lid-2}$, upon temperature rise from $T_1$ to $T_2$ (dotted line); then the addition of the thermo-thickening agent of the invention enables that the decrease of viscosity of the resulting solution upon temperature rise from $T_1$ to $T_2$ to be of less than x/2, from $\mu_{sol-1}$ to $\mu_{sol-2a}$ (solid lines). In one embodiment, in presence of the thermo-thickening agent, the decrease of viscosity is less than x/2 (solid line (a)). In a preferred embodiment, in presence of the thermo-thickening agent, the viscosity is maintained in a narrow range around the viscosity of the solution at $T_1$ (solid line (b)). In another specific embodiment, in presence of the thermo-thickening agent, the viscosity is increased above the viscosity of the solution at $T_1$ (solid line (c));

"Thermosetting resin": refers to a chemical compound in a viscous liquid that after curing induced by the action of heat or suitable radiation, changes irreversibly into an infusible and insoluble polymer network;

"Aryl": refers to a polyunsaturated, aromatic hydrocarbyl group having a single ring or multiple aromatic rings fused together (such as naphtyl) or linked covalently, typically containing 5 to 20, and preferably 6 to 12, carbon atoms having one or more aromatic rings among which it is possible to cite the phenyl group, the biphenyl group, the 1-naphthyl group, the 2-naphthyl group, the tetrahydronaphthyl group, the indanyl group and the binaphthyl group. In the present invention, the term "aryl" preferably refers to a single ring;

"Alkenyl": refers to a linear or branched hydrocarbon chain having at least one double bond, preferably linear hydrocarbon chain having at least one double bond. According to one embodiment, alkenyl refers to a $C_6$-$C_{18}$ alkenyl, preferably a linear $C_6$-$C_{18}$ alkenyl chain. According to one embodiment, alkenyl refers to a $C_8$, $C_9$, $C_{10}$, $C_{11}$, $C_{12}$, $C_{13}$, $C_{14}$, $C_{15}$ or $C_{16}$ alkenyl, preferably a linear $C_8$, $C_9$, $C_{10}$, $C_{11}$, $C_{12}$, $C_{13}$, $C_{14}$, $C_{15}$ or $C_{16}$ alkenyl chain;

"Alkynyl": refers to a linear or branched hydrocarbon chain having at least one triple bond, preferably linear hydrocarbon chain having at least one triple bond. According to one embodiment, alkynyl refers to a $C_6$-$C_{18}$ alkynyl, preferably a linear $C_6$-$C_{18}$ alkynyl chain. According to one embodiment, alkynyl refers to a $C_8$, $C_9$, $C_{10}$, $C_{11}$, $C_{12}$, $C_{13}$, $C_{14}$, $C_{15}$ or $C_{16}$ alkynyl, preferably a linear $C_8$, $C_9$, $C_{10}$, $C_{11}$, $C_{12}$, $C_{13}$, $C_{14}$, $C_{15}$ or $C_{16}$ alkynyl chain;

"Alkyl": refers to a hydrocarbyl radical of formula $C_nH_{2n+1}$ wherein n is a number greater than or equal to 1. Generally, alkyl groups of this invention comprise from 1 to 20 carbon atoms. Alkyl groups may be linear or branched and may be substituted as indicated herein. When a subscript is used herein following a carbon atom, the subscript refers to the number of carbon atoms that the named group may contain. Thus, for example, $C_1$-$C_4$ alkyl means an alkyl of one to four carbon atoms. $C_1$-$C_{20}$ alkyl includes all linear, or branched alkyl groups with between 1 and 20 carbon atoms, and thus includes methyl, ethyl, n-propyl, i-propyl, butyl and its isomers (e.g. n-butyl, i-butyl and t-butyl); pentyl and its isomers, hexyl and its isomers, heptyl and its isomers, octyl and its isomers, nonyl and its isomers, decyl and its isomers, undecyl and its isomers, dodecyl and its isomers, tridecyl and its isomers, tetradecyl and its isomers, pentadecyl and its isomers, hexadecyl and its isomers, heptadecyl and its isomers, octodecyl and its isomers, nonadecyl and its isomers, eicosyl and its isomers. According to one embodiment, alkyl refers to a linear hydrocarbyl radical of formula $C_nH_{2n+1}$ wherein n is a number greater than or equal to 1. According to one embodiment, alkyl refers to a $C_6$-$C1_8$ alkyl, preferably a linear $C_6$-$C1_8$ alkyl chain. According to one embodiment, alkyl refers to a $C_8$, $C_9$, $C_{10}$, $C_{11}$, $C_{12}$, $C_{13}$, $C_{14}$, $C_{15}$ or $C_{16}$ alkyl, preferably a linear $C_8$, $C_9$, $C_{10}$, $C_{11}$, $C_{12}$, $C_{13}$, $C_{14}$, $C_{15}$ or $C_{16}$ alkyl chain;

"Alkylaryl": refers to an aryl group substituted by an alkyl group, which may be represented as alkyl-aryl-;

"Alkylheteroaryl": refers to a heteroaryl group substituted by an alkyl group, which may be represented as alkyl-heteroaryl-;

"Alkoxy": refers to any —O-alkyl or —O-aryl group;

"Amide": refers to the moieties —CO—NRR' or —NR—CO—R', wherein R and R' represent preferably H, alkyl or aryl. According to a specific embodiment, "amide" refers to the —CO—$NH_2$ moiety;

"Amino": refers to any compound derived from ammoniac $NH_3$ by substitution of one or more hydrogen atoms with an organic radical. Amino preferably refers to —$NH_2$, —NHR and —NRR' wherein R and R' are preferably alkyl groups. Therefore "amino" includes alkylamino groups: monoalkylamino and dialkylamino;

"Arylalkyl": refers to an alkyl group substituted by an aryl group, which may be represented as aryl-alkyl-;

"Carboxy": refers to —COOH;

"Cold flow property": refers to ability for a fluid or semi-fluid to flow at a temperature equal or lower to room temperature (i.e. about 25° C.);

"Fuel": refers to any product for supplying energy to a heat engine;

"Grease": refers to any product under the form of a semifluid to solid product obtained by dispersing a thickening or gelling agent in an oil (or lubricant);

"Halo": refers to halogen atom selected from fluoro (—F), chloro (—Cl), bromo (—Br) and iodo (—I) atoms. In the present invention, the terms "terminal halo" refer to one or more halo atoms linked to a terminal carbon atom;

"Heteroaryl": refers to an aryl group as defined above, comprising at least one heteroatom, preferably chosen among O, N or S;

"Heteroarylalkyl": refers to an alkyl group substituted by an heteroaryl group, which may be represented as heteroaryl-alkyl-;

"Heteroalkylaryl": refers to an aryl group substituted by an heteroalkyl group, which may be represented as heteroalkyl-aryl-;

"Heteroalkenyl": refers to an alkenyl group as defined above, comprising at least one heteroatom, preferably chosen among O, N or S;

"Heteroalkynyl": refers to an alkynyl group as defined above, comprising at least one heteroatom, preferably chosen among O, N or S;

"Heteroalkyl": refers to an alkyl group as defined above, comprising at least one heteroatom, preferably chosen among O, N or S;

"Hydroxyl" or "hydroxy": refers to —OH;

"Imidazole": refers to an aromatic heterocyclic compound of formula $C_3H_4N_2$;

"Liquid": refers to any medium having a viscosity measured at room temperature in a range from 0.001 to 1000 Pa·s;

"Monomer": refers to a molecule that form the basic repeating unit for polymer. The term "monomer" refers to a compound having at least one chemical function able to be engaged in a polymerization reaction;

"Non-polar" or "apolar": refers to any chemical compound having a resulting dipolar moment ranging from 0 to 15;

"Oil" or "lubricant": refers to any fatty substance, liquid at room temperature and insoluble in water. In the present invention, these terms refer to any fatty substance that may be obtained from plants, minerals or animals;

"Oxo": refers to a —(C═O)— group;

"Perfume": refers to a substance able to emit and diffuse a fragrant odor;

"Pyrrolidine": refers to a heterocyclic compound of formula $C_4H_9N$;

"Urea": refers to a —NH—CO—NH— group;

"Spacer": refers to a chemical group (in the present invention referred to as Y) that separate two chemical function, herein two urea functions;

"Stereogenic center": refers to any atom comprising substituents being in a spatial arrangement which is not superimposable on its mirror image. In the present invention, the terms "stereogenic center" also refer to a carbon atom having 4 different substituents;

"Thiol": refers to a —SH moiety; and

"Thioxo": refers to a —(C═S)— group.

DETAILED DESCRIPTION

Compounds

The present invention relates to a compound of general formula (I):

(I)

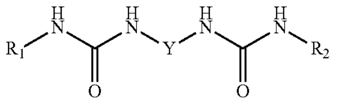

wherein:

Y represents aryl or heteroaryl, the aryl or heteroaryl group being optionally substituted by at least one group selected from alkyl, heteroalkyl, alkoxy, amino, alkylamino and halo; preferably Y represents a phenyl group optionally substituted by at least one group selected from $C_1$-$C_4$ alkyl, $C_1$-$C_4$ heteroalkyl, $C_1$-$C_4$ alkoxy, $C_1$-$C_4$ dialkylamino and halo; more preferably Y represents a phenyl group substituted by at least one $C_1$-$C_4$ alkyl or halo group; and $R_1$ and $R_2$ are each independently selected from H, alkyl, heteroalkyl, alkyloxycarbonylalkyl, alkyloxythiocarbonylalkyl. alkylthioxothiocarbonylalkyl and macromolecular groups, said groups being optionally substituted by at least one group selected from alkyl, heteroalkyl, alkenyl, heteroalkenyl, aryl, heteroaryl, alkylaryl, alkynyl, heteroalkynyl arylalkyl, heteroarylalkyl, alkylheteroaryl, alkoxy, alkylthio, oxo and thioxo group; said substituents being optionally substituted by one or more group selected from guanidine, aryl, pyrrolidine, imidazole, hydroxyaryl, carboxy, selanyl, hydroxyl, amide, thiol, alkylthio, amino, deuterium or halo.

According to one embodiment, Y is aryl. According to one embodiment, Y is heteroaryl. According to one embodiment, Y is a phenyl group. According to one embodiment, Y is phenyl group linked to two urea functions at positions 1 and 3:

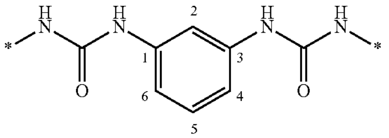 [SMILES: *NC(=O)Nc1cccc(NC(=O)N*)c1]

According to one embodiment, Y is a 2,4,6-substituted phenyl group. According to one embodiment, Y is a 4,6-substituted phenyl group. According to one embodiment, Y is a 2,6-substituted phenyl group. According to one embodiment, Y is a 2,4-substituted phenyl group. According to one embodiment, Y is a 2-substituted phenyl group. According to one embodiment, Y is a 4-substituted phenyl group. According to one embodiment, Y is a 6-substituted phenyl group.

According to one embodiment, Y is tolyl (i.e. a phenyl group substituted by one methyl). According to one embodiment, Y is xylyl (i.e. a phenyl group substituted by two methyl). According to one embodiment, Y is mesityl (i.e. a phenyl group substituted by three methyl). According to one embodiment, Y is a phenyl group substituted by one or more halo (i.e. fluoro (—F), chloro (—Cl), bromo (—Br) or iodo (—I) atom); preferably Y is a phenyl group substituted by two halo. According to one embodiment, Y is a phenyl group substituted by one halo. According to one embodiment, Y is a phenyl group substituted by two halo. According to one preferred embodiment, Y is a phenyl group substituted by two chloro atoms. According to one embodiment, Y is a 2,4,6-halo substituted phenyl group.

According to one embodiment, $R_1$ and $R_2$ are macromolecular chains; preferably selected from polyacrylates, polymethacrylates, polyolefins, polycarbonates, polyether, polydienes, polysiloxanes, polyesters, polynorborenes, polycyclooctenes and polystyrenes. In the present invention, “macromolecular chains” or “polymer chains” refer to chains having a high molecular weight and resulting from the multiple repetition of a repeating unit (monomer); said monomers being covalently linked each other. According to another embodiment, $R_1$ and $R_2$ are not macromolecular chains. According to one embodiment, $R_1$ and $R_2$ are not polymer chains. According to one embodiment, $R_1$ and $R_2$ are identical. According to one embodiment, $R_1$ and $R_2$ are different. According to one embodiment, $R_1$ and $R_2$ are each independently selected from linear alkyl or linear heteroalkyl chains, said chains being optionally substituted by one or more oxo, thioxo and/or halo groups.

According to one embodiment, $R_1$ and $R_2$ are each independently selected from H, alkyl, heteroalkyl, alkyloxycarbonylalkyl, alkyloxythiocarbonylalkyl and alkylthioxothiocarbonylalkyl, said groups being optionally substituted by at least one group selected from alkyl, heteroalkyl, alkenyl, heteroalkenyl, aryl, heteroaryl, alkylaryl, alkynyl, heteroalkynyl arylalkyl, heteroarylalkyl, alkylheteroaryl, alkoxy, alkylthio, oxo and thioxo group; said substituents being optionally substituted by one or more group selected from guanidine, aryl, pyrrolidine, imidazole, hydroxyaryl, carboxy, selanyl, hydroxyl, amide, thiol, alkylthio, amino, deuterium or halo.

According to one embodiment, preferred compound of formula (I) are compounds of formula (Ibis):

(Ibis)

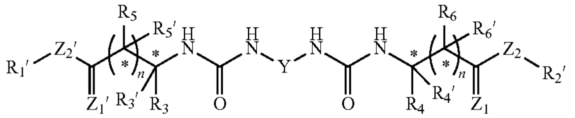

wherein:

Y is as defined above;

$R_1'$ and $R_2'$ are each independently selected from linear alkyl, heteroalkyl, alkenyl, heteroalkenyl, alkynyl and heteroalkynyl group, optionally substituted by one or more halo; preferably $R_1'$ and $R_2'$ are each independently selected from linear alkyl or heteroalkyl group, said linear group being optionally substituted by one or more halo; more preferably $R_1'$ and $R_2'$ are each independently selected from linear $C_6$-$C_{18}$ alkyl or heteroalkyl group, said linear group being optionally substituted by one or more terminal halo;

$R_3'$, $R_3$, $R_4$, $R_4'$ $R_5'$, $R_5$, $R_6$ and $R_6'$ are each independently selected from H, alkyl, alkenyl, aryl, heteroalkyl, heteroalkenyl, heteroaryl, alkylaryl, arylalkyl, heteroarylalkyl or alkylheteroaryl, optionally substituted by guanidine, aryl, pyrrolidine, imidazole, hydroxyaryl, carboxy, selanyl, hydroxyl, amide, thiol, alkylthio, amino, deuterium or halo; preferably $R_3'$, $R_3$, $R_4$, $R_4'$ $R_5'$, $R_5$, $R_6$ and $R_6'$ are each independently selected from H, $C_1$-$C_{12}$ alkyl substituted by at least one aryl, said aryl being optionally substituted by one or more halo or deuterium;

$Z_1$, $Z_1'$, $Z_2$ and $Z_2'$ are each independently selected from O or S atoms;

n represents a positive integer from 0 to 10; preferably n is equal to 0; and optionally * stands for a stereogenic center.

According to one embodiment, when $R_3$ and $R_3'$ are different, * represents a stereogenic center. According to one embodiment, when $R_4$ and $R_4'$ are different, * represents a stereogenic center. According to one embodiment, when $R_5$ and $R_5'$ are different, * represents a stereogenic center. According to one embodiment, when $R_6$ and $R_6'$ are different, * represents a stereogenic center.

According to one embodiment, $R_3'$, $R_3$, $R_4$, $R_4'$ $R_5'$, $R_5$, $R_6$ and $R_6'$ are each independently selected from H, guanidinealkyl, imidazolealkyl, aminoalkyl, carboxyalkyl, hydroxyalkyl, amidoalkyl, thioalkyl, selanylalkyl, pyrrolidinalkyl, phenylalkyl, benzylalkyl, hydroxyphenylalkyl, hydroxybenzylalkyl and indolylalkyl.

According to one embodiment, preferred compound of formula (Ibis) are compounds of formula (Iter):

(Iter)

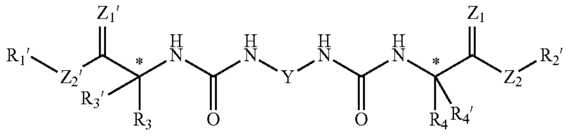

wherein:

Y, $R_1'$, $R_2'$ $R_3'$, $R_3$, $R_4$, $R_4'$ $Z_1$, $Z_1'$, $Z_2$, $Z_2'$ and * are as defined above.

According to one embodiment, the compound of the invention is enantiopure (i.e. the compound of the invention is a single isomer with one chirality). According to one embodiment, the compound of the invention is R,R-enantiomer. According to one embodiment, the compound of the invention is S,S-enantiomer. According to one embodiment, the compound of the invention is R,S-enantiomer. According to one embodiment, the compound of the invention is S,R-enantiomer. According to one embodiment, the compound of the invention is achiral. According to one embodiment, the compound of the invention is racemic. According to one embodiment, the compound of the invention is a mixture of diastereoisomers.

According to one embodiment, preferred compound of formula (I) are compounds of formula (II):

(II)

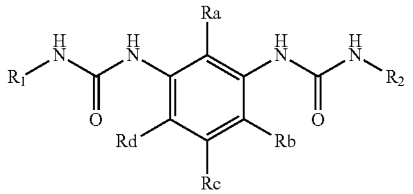

wherein:

$R_a$, $R_b$, $R_c$ and $R_d$ are each independently selected from H, alkyl, heteroalkyl, alkoxy, amino, alkylamino and halo; preferably $R_b$ and $R_d$ are each independently selected from H, $C_1$-$C_4$ alkyl, $C_1$-$C_4$ heteroalkyl, $C_1$-$C_4$ alkoxy, $C_1$-$C_4$ dialkylamino and halo; more preferably $R_b$ and $R_d$ are each independently selected from at least one $C_1$-$C_4$ alkyl or halo; and $R_1$ and $R_2$ are as defined above.

According to one embodiment, $R_a$ and $R_c$ are both H. According to one embodiment, $R_a$, $R_b$, $R_c$ and $R_d$ are not all H. According to one embodiment, $R_b$ and $R_d$ are not both H. According to one embodiment, at least one of $R_b$ and $R_d$ is not H.

According to one embodiment, the compound of formula (II) is ethylhexylureidoxylene (EHUX), also named ethylhexylureido-4,6-dimethylbenzene, of formula:

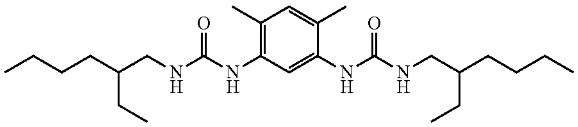

EHUX

According to an alternative embodiment, the compound of formula (II) is not EHUX. According to one embodiment, the compound of formula (II) is not EHUT, also named ethylhexylureidotoluene, of formula:

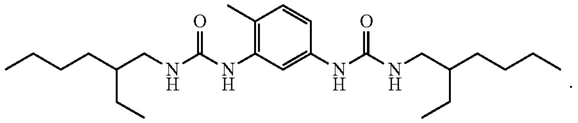

EHUT

According to one embodiment, the compound of formula (II) is not EHUTMB, also named ethylhexylureidotrimethylbenzene, of formula:

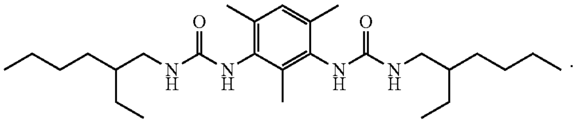 [SMILES: CCCCC(CC)CNC(=O)Nc1c(C)cc(C)c(NC(=O)NCC(CC)CCCC)c1C]

According to one embodiment, preferred compound of formula (II) are compounds of formula (III):

(III)

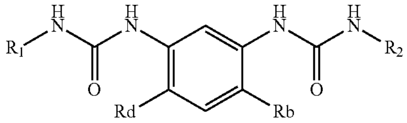

wherein:

$R_b$, $R_c$, $R_1$ and $R_2$ are as defined above.

The present invention also refers to compounds of general formula (IV):

(IV)

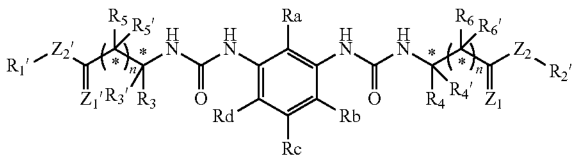

wherein:

$R_a$, $R_b$, $R_c$ and $R_d$ are as defined in formula (II);

$R_1'$ and $R_2'$ are each independently selected from linear alkyl, heteroalkyl, alkenyl, heteroalkenyl, alkynyl, heteroalkynyl and macromolecular groups, optionally substituted by one or more halo; preferably $R_1'$ and $R_2'$ are each independently selected from linear alkyl or linear heteroalkyl group, said linear group being optionally substituted by one or more halo; more preferably $R_1'$ and $R_2'$ are each independently selected from linear $C_6$-$C_{18}$ alkyl or heteroalkyl group, said linear group being optionally substituted by one or more terminal halo;

$R_3'$, $R_3$, $R_4$, $R_4'$ $R_5'$, $R_5$, $R_6$ and $R_6'$ are each independently selected from H, alkyl, alkenyl, aryl, heteroalkyl, heteroalkenyl, heteroaryl, alkylaryl, arylalkyl, heteroarylalkyl or alkylheteroaryl, optionally substituted by guanidine, aryl, pyrrolidine, imidazole, hydroxyaryl, carboxy, selanyl, hydroxyl, amide, thiol, alkylthio, amino, deuterium or halo; preferably $R_3'$, $R_3$, $R_4$, $R_4'$ $R_5'$, $R_5$, $R_6$ and $R_6'$ are each independently selected from H, $C_1$-$C_{12}$ alkyl substituted by at least one aryl, said aryl being optionally substituted by one or more halo or deuterium;

$Z_1$ and $Z_1'$ are each independently selected from O and S atoms;

$Z_2$ and $Z_2'$ are each independently selected from —NH—, O and S atoms;

n represents a positive integer from 0 to 10; preferably n is equal to 0; and optionally, * stands for a stereogenic center.

According one embodiment, $R_1'$ and $R_2'$ are each independently selected from linear alkyl, heteroalkyl, alkenyl, heteroalkenyl, alkynyl and heteroalkynyl group, optionally substituted by one or more halo; preferably $R_1'$ and $R_2'$ are each independently selected from linear alkyl or linear heteroalkyl group, said linear group being optionally substituted by one or more halo; more preferably $R_1'$ and $R_2'$ are each independently selected from linear $C_6$-$C_{18}$ alkyl or heteroalkyl group, said linear group being optionally substituted by one or more terminal halo. According one embodiment, $R_1'$ and $R_2'$ are each independently selected from linear $C_6$-$C_{18}$ alkyl, $C_6$-$C_{18}$ heteroalkyl, $C_6$-$C_{18}$ alkenyl, $C_6$-$C_{18}$ heteroalkenyl, $C_6$-$C_{18}$ alkynyl, heteroalkynyl and macromolecular groups, optionally substituted by one or more halo. According one embodiment, $R_1'$ and/or $R_2'$ are not selected from $C_1$-$C_5$ alkyl, $C_1$-$C_5$ heteroalkyl, $C_1$-$C_5$ alkenyl, $C_1$-$C_5$ heteroalkenyl, and $C_1$-$C_5$ alkynyl, heteroalkynyl. According one embodiment, $R_1'$ and/or $R_2'$ are not selected from methyl, ethyl, propyl, butyl, or pentyl group.

According one embodiment, $R_b$ and $R_d$ are not both a hydrogen atom (—H). According one embodiment, at least one of $R_b$ and $R_d$ does not represent a hydrogen atom (—H).

According one embodiment, preferred compounds of general formula (IV) are compounds of formula (IV bis):

(IVbis)

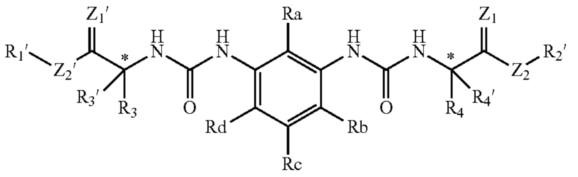

wherein $R_a$, $R_b$, $R_c$, $R_d$, $R_1'$, $R_2'$, $R_3'$, $R_3$, $R_4$ and $R_4'$ are as defined in formula (IV).

According to one embodiment, preferred compounds of formula (IVbis) are compounds of formula (IVter):

(IVter)

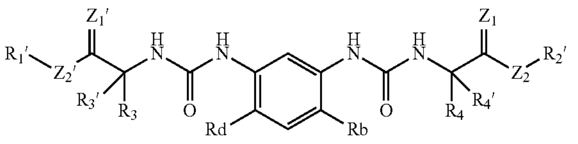

wherein $R_b$, $R_d$, $R_1'$, $R_2'$, $R_3'$, $R_3$, $R_4$ and $R_4'$ are as defined in formula (IV).

According to one embodiment, $R_b$ and $R_d$ are each independently selected from H, alkyl, heteroalkyl, alkoxy, amino, alkylamino and halo; preferably $R_b$ and $R_d$ are each independently selected from H, $C_1$-$C_4$ alkyl, $C_1$-$C_4$ heteroalkyl, $C_1$-$C_4$ alkoxy, $C_1$-$C_4$ dialkylamino and halo; more preferably $R_b$ and $R_d$ are each independently selected from at least one $C_1$-$C_4$ alkyl or halo.

According to one embodiment, $R_{1'}$ and $R_{2'}$ are linear alkyl or linear heteroalkyl chains. According to one embodiment, $R_{1'}$ and $R_{2'}$ are not ramified chains.

According to one embodiment, $Z_1$, $Z_1'$, $Z_2$ and $Z_2'$ represent O atoms. According to one embodiment, $Z_1$, $Z_1'$, $Z_2$ and $Z_2'$ represent S atoms. According to one embodiment, $Z_1$, $Z_1'$, $Z_2$ and $Z_2'$ represent S atoms. According to one embodiment, $Z_1$, and $Z_1'$ represent O atoms, and $Z_2$ and $Z_2'$ represent S atoms. According to one embodiment, $Z_1$, and $Z_1'$ represent S atoms, and $Z_2$ and $Z_2'$ represent O atoms.

According to one embodiment, compounds of general formula (IV) are symmetric. According to one embodiment, compounds of general formula (IV) are non-symmetric.

According to one embodiment, preferred compound of formula (IVter) are compounds of formula (V-a):

(V-a)

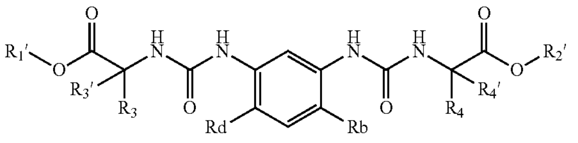

wherein $R_b$, $R_d$, $R_1'$, $R_2'$, $R_3'$, $R_3$, $R_4$ and $R_4'$ are as defined above.

In the present invention, compounds of formula (V-a) are called "ester bis-ureas".

According to one embodiment, preferred compound of formula (IVter) are compounds of formula (V-b):

(V-b)

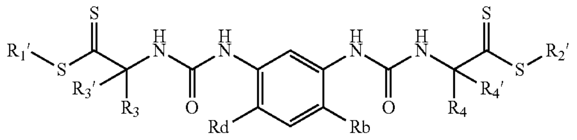

wherein $R_b$, $R_d$, $R_1'$, $R_2'$, $R_3'$, $R_3$, $R_4$ and $R_4'$ are as defined above.

In the present invention, compounds of formula (V-b) are called "dithioester bis-ureas".

According to one embodiment, preferred compound of formula (IVter) are compounds of formula (V-c):

(V-c)

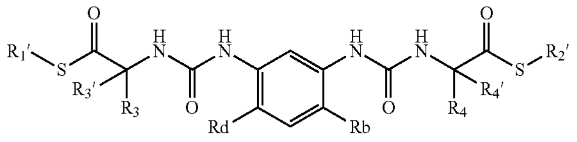

wherein $R_b$, $R_d$, $R_1'$, $R_2'$, $R_3'$, $R_3$, $R_4$ and $R_4'$ are as defined above.

In the present invention, compounds of formula (V-c) are called "thioester bis-ureas".

According to one embodiment, preferred compound of formula (IVter) are compounds of formula (V-d):

(V-d)

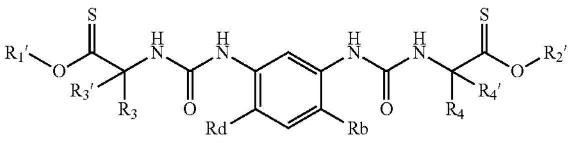

wherein $R_b$, $R_d$, $R_1'$, $R_2'$, $R_3'$, $R_3$, $R_4$ and $R_4'$ are as defined above.

In the present invention, compounds of formula (V-d) are called "thionoester bis-ureas".

According to one embodiment, preferred compounds of the invention are those listed in Table 1 hereafter:

TABLE 1

| Cpd reference | Structure | Name |
|---|---|---|
| H3C5Tol | 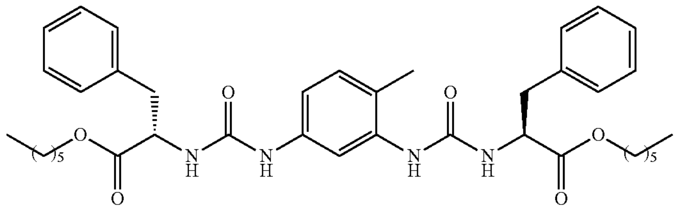 | (2S,2'S)-dihexyl 2,2'-((((4-methyl-1,3-phenylene)bis(azanediyl))bis(carbonyl))bis(azanediyl))bis(3-phenylpropanoate) |
| H3C6Tol | 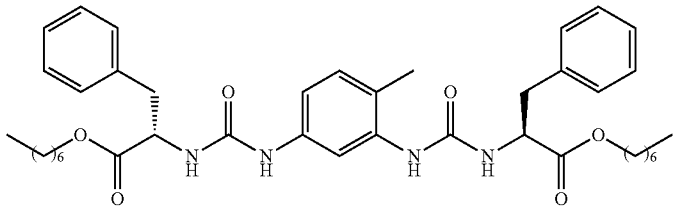 | (2S,2'S)-diheptyl 2,2'-((((4-methyl-1,3-phenylene)bis(azanediyl))bis(carbonyl))bis(azanediyl))bis(3-phenylpropanoate) |
| H3C7Tol | 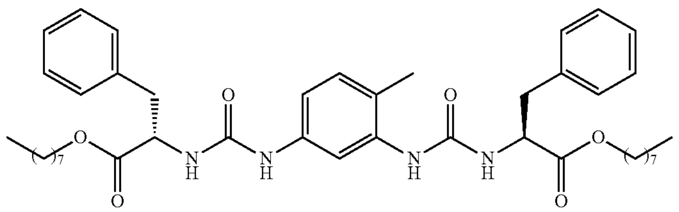 | (2S,2'S)-dioctyl 2,2'-((((4-methyl-1,3-phenylene)bis(azanediyl))bis(carbonyl))bis(azanediyl))bis(3-phenylpropanoate) |
| H3C7Xyl | 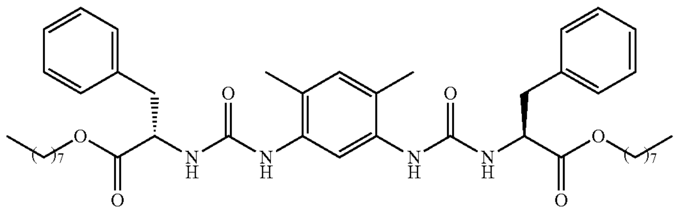 | (2S,2'S)-dioctyl 2,2'-((((4,6-dimethyl-1,3-phenylene)bis(azanediyl))bis(carbonyl))bis(azanediyl))bis(3-phenylpropanoate) |

TABLE 1-continued

| Cpd reference | Structure | Name |
|---|---|---|
| H3C7Cl | 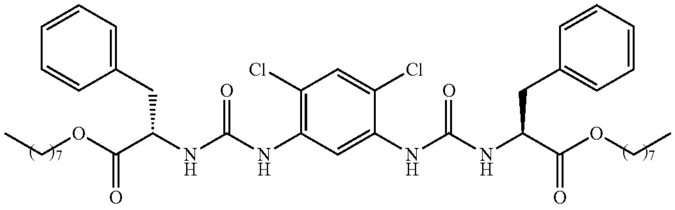 | (2S,2'S)-dioctyl 2,2'-((((4,6-dichloro-1,3-phenylene)bis(azanediyl))bis(carbonyl))bis(azanediyl))bis(3-phenylpropanoate) |
| H3C8Tol | 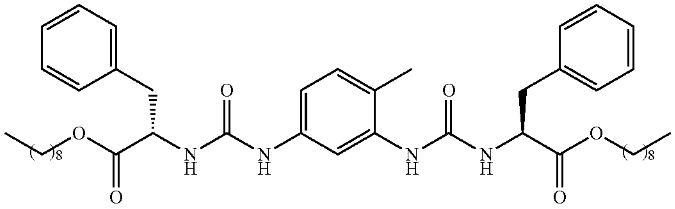 | (2S,2'S)-dinonyl 2,2'-((((4-methyl-1,3-phenylene)bis(azanediyl))bis(carbonyl))bis(azanediyl))bis(3-phenylpropanoate) |
| H3C8Xyl | 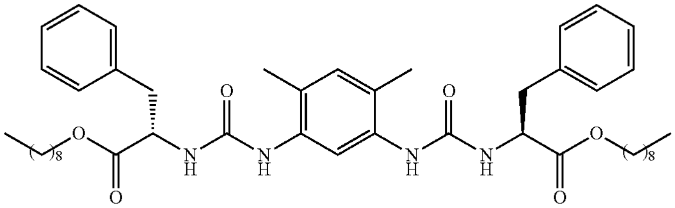 | (2S,2'S)-dinonyl 2,2'-((((4,6-dimethyl-1,3-phenylene)bis(azanediyl))bis(carbonyl))bis(azanediyl))bis(3-phenylpropanoate) |
| H3C9Tol | 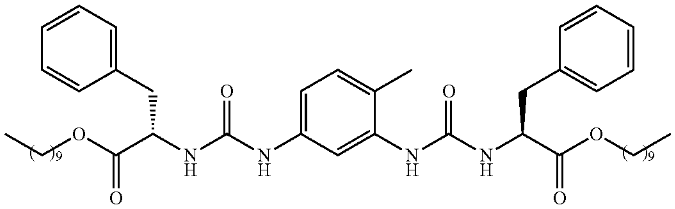 | (2S,2'S)-didecyl 2,2'-((((4-methyl-1,3-phenylene)bis(azanediyl))bis(carbonyl))bis(azanediyl))bis(3-phenylpropanoate) |
| H3C10Tol | 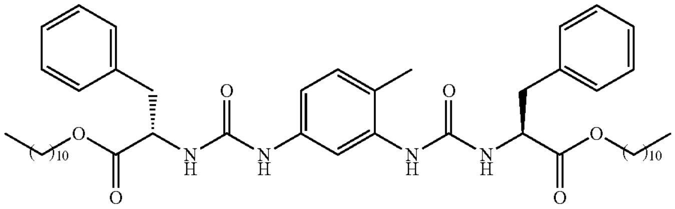 | (2S,2'S)-diundecyl 2,2'-((((4-methyl-1,3-phenylene)bis(azanediyl))bis(carbonyl))bis(azanediyl))bis(3-phenylpropanoate) |
| H3C11Tol | 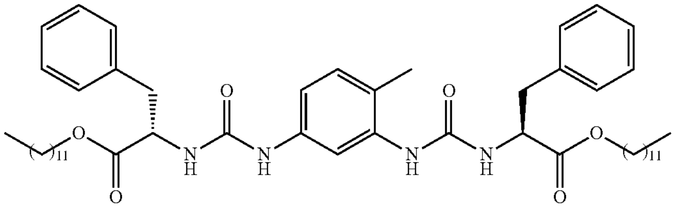 | (2S,2'S)-didodecyl 2,2'-((((4-methyl-1,3-phenylene)bis(azanediyl))bis(carbonyl))bis(azanediyl))bis(3-phenylpropanoate) |
| H3C11Xyl | 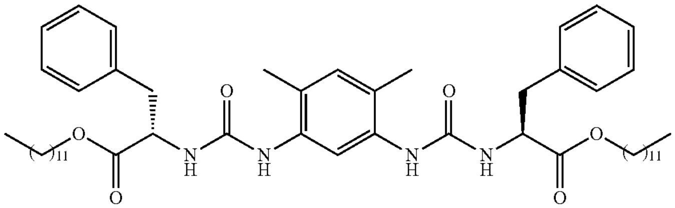 | (2S,2'S)-didodecyl 2,2'-((((4,6-dimethyl-1,3-phenylene)bis(azanediyl))bis(carbonyl))bis(azanediyl))bis(3-phenylpropanoate) |

TABLE 1-continued

| Cpd reference | Structure | Name |
|---|---|---|
| H3C12Tol | 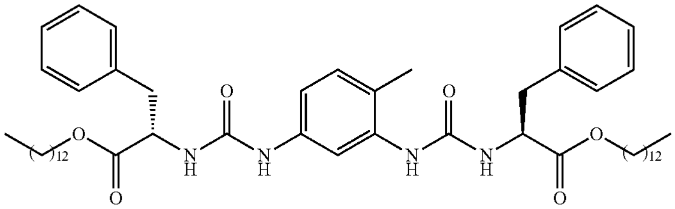 | (2S,2'S)-ditridecyl 2,2'-((((4-methyl-1,3-phenylene)bis(azanediyl))bis(carbonyl))bis(azanediyl))bis(3-phenylpropanoate) |
| H3C13Tol | 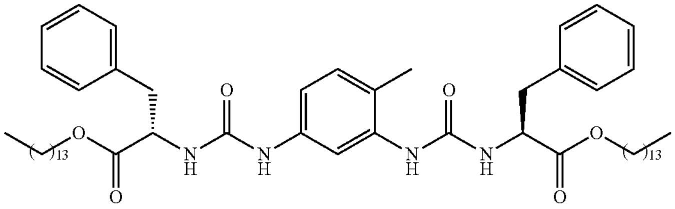 | (2S,2'S)-ditetradecyl 2,2'-((((4-methyl-1,3-phenylene)bis(azanediyl))bis(carbonyl))bis(azanediyl))bis(3-phenylpropanoate) |
| H3C15Tol | 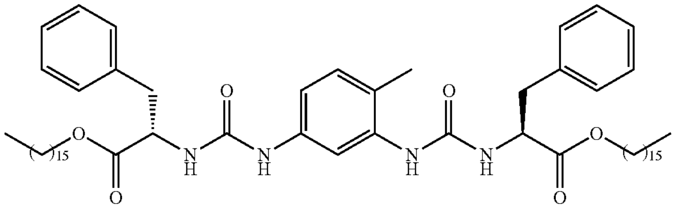 | (2S,2'S)-dihexadecyl 2,2'-((((4-methyl-1,3-phenylene)bis(azanediyl))bis(carbonyl))bis(azanediyl))bis(3-phenylpropanoate) |
| H3C15Xyl | 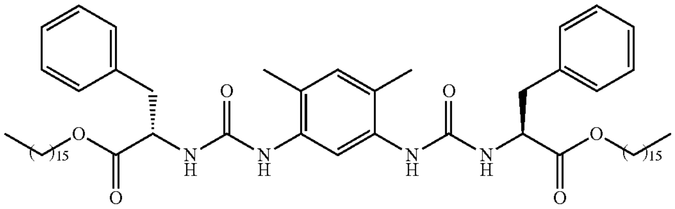 | (2S,2'S)-dihexadecyl 2,2'-((((4,6-dimethyl-1,3-phenylene)bis(azanediyl))bis(carbonyl))bis(azanediyl))bis(3-phenylpropanoate) |
| H3C17Tol | 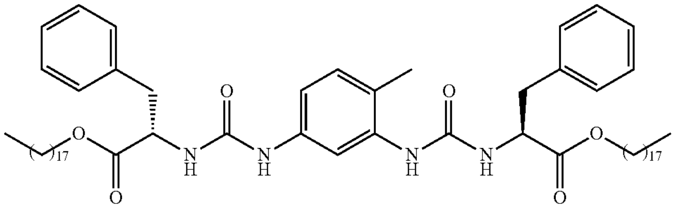 | (2S,2'S)-dioctadecyl 2,2'-((((4-methyl-1,3-phenylene)bis(azanediyl))bis(carbonyl))bis(azanediyl))bis(3-phenylpropanoate) |
| H3C7d$_5$-PheTol | 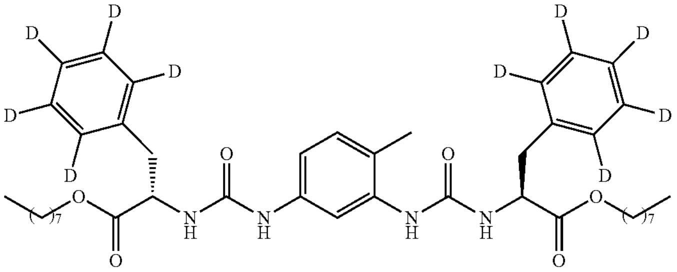 | (2S,2'S)-dioctyl 2,2'-((((4-methyl-1,3-phenylene)bis(azanediyl))bis(carbonyl))bis(azanediyl))bis(3-pentadeuteriumphenylpropanoate) |
| Br3C11Tol | 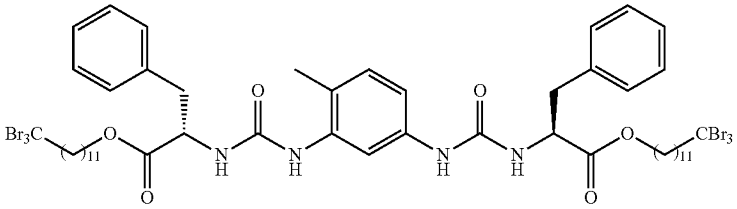 | (2S,2'S)-bis(12,12,12-tribromododecyl) 2,2'-((((4-methyl-1,3-phenylene)bis(azanediyl))bis(carbonyl))bis(azanediyl))bis(3-phenylpropanoate) |

TABLE 1-continued

| Cpd reference | Structure | Name |
|---|---|---|
| Br3C11Xyl | 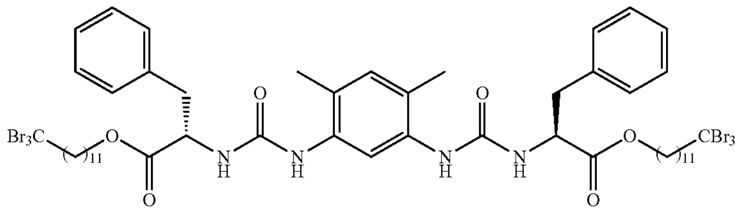 | (2S,2'S)-bis(12,12,12-tribromododecyl) 2,2'-((((4,6-dimethyl-1,3-phenylene)bis(azanediyl))bis(carbonyl))bis(azanediyl))bis(3-phenylpropanoate) |
| Br3C11Cl | 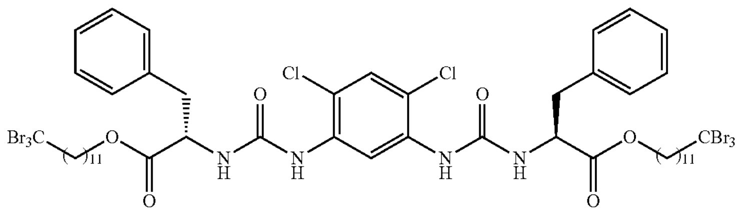 | (2S,2'S)-bis(12,12,12-tribromododecyl) 2,2'-((((4,6-dichloro-1,3-phenylene)bis(azanediyl))bis(carbonyl))bis(azanediyl))bis(3-phenylpropanoate) |
| Cl3C11Xyl | 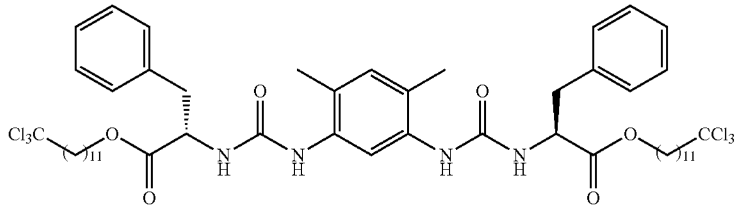 | (2S,2'S)-bis(12,12,12-trichlorododecyl) 2,2'-((((4,6-dimethyl-1,3-phenylene)bis(azanediyl))bis(carbonyl))bis(azanediyl))bis(3-phenylpropanoate) |

In Table 1, the term "Cpd" means compound.

The compounds of Table 1 were named using ChemBioDraw® Ultra version 12.0 (PerkinElmer).

Composition

The present invention also refers to a composition comprising at least one compound of the invention as defined above, and a non-polar liquid. Especially, the present invention refers to a composition comprising a non-polar liquid and at least one compound of formula (IV) or (IV bis) as defined above.

According to one embodiment, the composition comprises one single compound of the invention as defined above, and a non-polar liquid. According to one embodiment, the composition comprises two compounds of the invention as defined above, and a non-polar liquid.

According to one embodiment, the composition is constituted by a non-polar liquid and at least one compound of the invention as described above.

According to one embodiment, the composition is constituted by a non-polar liquid and at least one compound of formula (IV) or of formula (IV bis) as defined above.

According to one embodiment, the non-polar liquid is liquid or semi-liquid. According to one embodiment, the non-polar liquid is selected methylcyclohexane and dodecane. According to one embodiment, the non-polar liquid is selected from an oil (or lubricant), a grease, a monomer, a thermosetting resin, a perfume or a fuel.

According to one embodiment, the oil is selected from mineral (hydrocarbon), natural (fatty ester) or synthetic (poly(alpha olefin)) oils. According to one embodiment, the monomer selected from acrylates, methacrylates and styrenics.

In the present invention, the relative viscosity is measured by using Anton paar AMVn falling-ball microviscometer with a 0.16 mm diameter capillary. Three measurements are carried out at an angle of +20° and −20°. The viscosity value is reported as an average of those measurements.

According to one embodiment, the non-polar liquid when not comprising a compound of the invention, has a viscosity at room temperature ranging from 0.001 to 1000 Pa·s; preferably from 0.01 to 100 Pa·s. According to one embodiment, the non-polar liquid when not comprising a compound of the invention, has a viscosity at room temperature ranging from 1 to 100 Pa·s, preferably from 10 to 100 Pa·s, from 20 to 100 Pa·s, from 30 to 100 Pa·s, from 40 to 100 Pa·s, from 50 to 100 Pa·s, from 60 to 100 Pa·s, from 70 to 100 Pa·s, from 80 to 100 Pa·s, or from 90 to 100 Pa·s. According to one embodiment, the non-polar liquid when not comprising a compound of the invention, has a viscosity at room temperature ranging from 0.01 to 90 Pa·s, preferably from 0.01 to 80 Pa·s, from 0.01 to 70 Pa·s, from 0.01 to 60 Pa·s, from 0.01 to 50 Pa·s, from 0.01 to 40 Pa·s, from 0.01 to 30 Pa·s, from 0.01 to 20 Pa·s, from 0.01 to 10 Pa·s, or from 0.01 to 1 Pa·s.

According to one embodiment, the composition of the invention (i.e. the non-polar liquid comprising at least one compound of the invention) has a relative viscosity at room temperature ranging from 1 to 100; preferably from 1 to 10.

According to one embodiment, in the composition of the invention, the compound of the invention is at a concentration in the non-polar liquid, ranging from more than 0 to 5%; preferably from 0.01 to 1% by weight to the total weight of the composition. According to one embodiment, the concentration of the compound of the invention in the non-polar liquid is about 0.01% by weight to the total weight of the composition. According to one embodiment, in the composition of the invention, the compound of the invention is at a concentration in the non-polar liquid, ranging from 0.001 to 5%; preferably from 0.01 to 5%, from 0.1 to 5%, from 1 to 5%, from 2 to 5%, from 3 to 5%, from 4 to 5%, by weight to the total weight of the composition. According to one embodiment, in the composition of the invention, the compound of the invention is at a concentration in the non-polar liquid of 1, 2, 3, 4, or 5%, by weight to the total weight of the composition. According to one embodiment, the concentration of the compound of the invention in the non-polar liquid is about 0.01%, 0.02%, 0.03%, 0.04%, 0.05%, 0.06%, 0.07%, 0.08%, 0.09% or 1% by weight to the total weight of the composition.

According to one embodiment, the compound of the invention is at a molar concentration in the non-polar liquid, preferably in methylcyclohexane or dodecane, ranging from more than 0 to 50 mM; preferably from 0.1 to 10 mM. According to one embodiment, the concentration of the compound of the invention in the non-polar liquid is about 0.1 mM. According to one embodiment, the compound of the invention is at a molar concentration in the non-polar liquid, preferably in methylcyclohexane or dodecane, ranging from 0.01 to 50 mM, preferably from 0.01 to 50 mM, from 0.1 to 50 mM, from 1 to 50 mM, from 10 to 50 mM, from 20 to 50 mM, from 30 to 50 mM, or from 40 to 50 mM. According to one embodiment, the concentration of the compound of the invention in the non-polar liquid is from 0.1 to 10 mM, preferably from 1 to 10 mM, preferably from 2 to 10 mM, 3 to 10 mM, 4 to 10 mM, 5 to 10 mM, 6 to 10 mM, 7 to 10 mM, 8 to 10 mM or 9 to 10 mM. According to one embodiment, the concentration of the compound of the invention in the non-polar liquid is 1, 2, 3, 4, 5, 6, 7, 8, 9 or 10 mM.

According to one embodiment, the composition may further comprise suitable additives.

Process for Manufacturing Compounds of the Invention

The present invention also relates to a process for manufacturing compounds of formula (IVbis) as defined above wherein $Z_1$, $Z_1'$, $Z_2$ and $Z_2'$ represent O atom, comprising reacting at least one ester ammonium salt of formula (A-1):

(A-1)

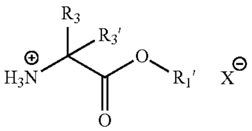

wherein $R_1'$, $R_3'$ and $R_3$, are as defined above; and $X^-$ is an anion, preferably selected from chloride, bromide, sulfate, hydrogenosulfate and sulfonate; more preferably $X^-$ is tosylate;

with (a) either diisocyanate of general formula (A-2):

(A-2)

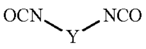

wherein Y is as defined above;

(b) or a mixture of reagents allowing the in situ preparation of diisocyanate of general formula (A-2).

According to one embodiment, the ester ammonium salt is an ester ammonium tosylate salt:

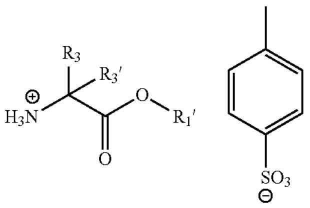

wherein $R_1'$, $R_3'$ and $R_3$, are as defined above;

According to one embodiment, the step (b) comprises the mixture of a compound having a carbonyl function and a diamine of formula (A-3):

(A-3)

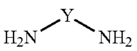

wherein Y is as defined above.

According to one embodiment, the ester ammonium salt is an ester ammonium tosylate salt:

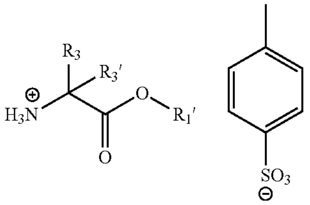

wherein $R_1'$, $R_3'$ and $R_3$, are as defined above.

According to one embodiment, the compound having a carbonyl function is selected from oxychlorides and carbonates.

According to one embodiment, the compound having a carbonyl function is phosgene:

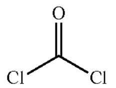

According to one embodiment, the compound having a carbonyl function is bis(trichloromethyl)carbonate:

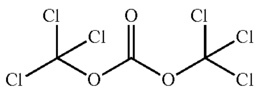 [SMILES: O=C(OC(Cl)(Cl)Cl)OC(Cl)(Cl)Cl]

According to one embodiment, compound A-2 is compound A-2bis:

(A-2bis)

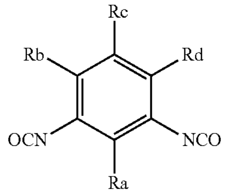

wherein $R_a$, $R_b$, $R_c$ and $R_d$ are as defined above.

According to one embodiment, compound A-2 is an aryl substituted by at least two isocyanato groups, preferably an alkyl benzene comprising two isocyanato groups; more preferably compound A-2 is 2,4-diisocyanato-1-methylbenzene.

According to one embodiment, compound A-3 is an aryl substituted by at least two amino groups, preferably an alkyl benzene comprising two amino groups. According to one embodiment, compound A-3 is of formula (A-3bis):

(A-3 bis)

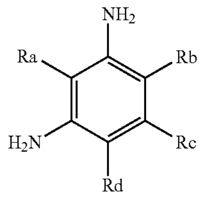

wherein $R_a$, $R_b$, $R_c$ and $R_d$, are as defined above.

According to one embodiment, the ester ammonium salt of formula (A-1) is synthetized in a preliminary step comprising reacting an amino acid and an alcohol.

According to one embodiment, the amino acid is selected from alanine (Ala), arginine (Arg), asparagine (Asn), aspartate (Asp), cysteine (Cys), glutamate (Glu), glutamine (Gln), glycine (Gly), histidine (His), isoleucine (Ile), leucine (Leu), lysine (Lys), methionine (Met), phenylalanine (Phe), proline (Pro), pyrrolysine, selenocysteine (Sec), serine (Ser), threonine (Thr), tryptophan (Trp), tyrosine (Tyr) and valine (Val); preferably glycine, valine, phenylalanine, tyrosine, histidine, tryptophan, iso-leucine and methionine. According to one embodiment, the amino acid is phenylalanine.

According to one embodiment, the alcohol is hydroxyalkane, preferably linear alkyl chains having a hydroxyl group. According to one embodiment, the preliminary step comprises reacting 1 equivalent of amino acid and 1.1 equivalent of alcohol.

According to one embodiment, the preliminary step further comprises a solvent, preferably a non-polar solvent; more preferably the solvent is toluene.

According to one embodiment, the preliminary step is carried out at a temperature higher than room temperature, preferably at a temperature ranging from 30° C. to 150° C. According to one embodiment, the preliminary step is carried out at a temperature higher than room temperature, preferably at a temperature ranging from 40° C. to 150° C., preferably from 50° C. to 150° C., from 60° C. to 150° C., from 70° C. to 150° C., from 80° C. to 150° C., from 90° C. to 150° C., from 100° C. to 150° C., from 110° C. to 150° C., from 120° C. to 150° C., from 130° C. to 150° C., or from 140° C. to 150° C. According to one embodiment, the preliminary step is carried out under reflux.

According to one embodiment, the preliminary step is carried out during a period time ranging from 1 h to 48 h, preferably from 1 h to 24 h, more preferably for 12 h. According to one embodiment, the preliminary step is carried out during a period time ranging from 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47 or 48 h.

Step (a)

According to one embodiment, the step (a) is carried out in a solvent, preferably an organic solvent, more preferably in tetrahydrofuran (THF).

According to one embodiment, the step (a) further comprises the use of an amine, preferably triethylamine.

Step (b)

According to one embodiment, the step (b) is carried out in a solvent, preferably an organic solvent, more preferably in dichloromethane (DCM).

According to one embodiment, the step (b) further comprises the use of an amine, preferably NN-Diisopropylethylamine (DIEA).

Uses

As mentioned above, the present invention relates to the use as a thermo-thickening agent of a compound or a composition of the invention as defined above.

Especially, the present invention refers to the use as a thermo-thickening agent of a compound of general formula (I):

(I)

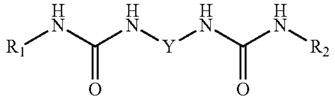

wherein Y, $R_1$ and $R_2$ are as defined above.

According to one embodiment, the compound is of general formula (II):

(II)

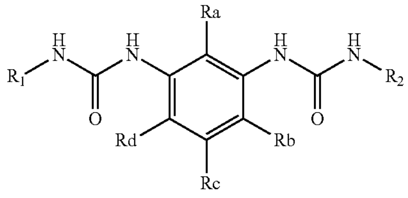

wherein $R_1$, $R_2$ $R_a$, $R_b$, $R_c$ and $R_d$ are as defined above.

Especially, the present invention refers to the use as a thermo-thickening agent of a compound of general formula (IV) and/or formula (IVbis) as defined above.

According to one embodiment, the compound or the composition of the invention is useful for thermo-thickening a non-polar liquid; preferably an oil (or lubricant), a grease, a monomer, a thermosetting resin, a perfume or a fuel.

According to one embodiment, the compound or the composition of the invention is useful (a) for thickening a non-polar liquid at a temperature ranging from 0° C. to 50° C., preferably from 20° C. to 45° C., and/or for maintaining the viscosity obtained at step (a) when the temperature increases. According to one embodiment, the compound or the composition of the invention is useful (a) for thickening a non-polar liquid at a temperature ranging from 0° C. to 50°

C., preferably from 20° C. to 45° C., and/or for maintaining the viscosity obtained at step (a) when the temperature is higher from 50° C., preferably ranges from 50° C. to 100° C. According to one embodiment, the compound or the composition of the invention is useful (a) for thickening a non-polar liquid at a temperature ranging from 0° C. to 50° C., preferably from 20° C. to 45° C., and/or for avoiding that, upon temperature rise at temperature higher than 50° C., the viscosity obtained at step (a) decreases to the same extend than it decreases in absence of any thermo-thickening agent.

According to one embodiment, the compound or the composition of the invention is useful for thermo-thickening at a temperature ranging from 5° C. to 100° C.; preferably from 10° C. to 60° C.; more preferably from 20° C. to 50° C. According to one embodiment, the compound or the composition of the invention is useful for thermo-thickening at a temperature ranging from 10° C. to 100° C., preferably from 20° C. to 100° C., 30° C. to 100° C., 40° C. to 100° C., 50° C. to 100° C., 60° C. to 100° C., 70° C. to 100° C., 80° C. to 100° C., or 90° C. to 100° C. According to one embodiment, the compound or the composition of the invention is useful for thermo-thickening at a temperature of 20, 25, 30, 35, 40, 45 or 50° C.

According to one embodiment, the compound or the composition of the invention is further useful for improving the cold flow property of a non-polar liquid. According to one embodiment, the compound or the composition of the invention is useful for improving the cold flow property of a non-polar liquid. According to one embodiment, the compound or the composition of the invention is useful for maintaining and/or increasing the viscosity of a non-polar liquid during its heating.

Advantageously, the compounds or composition of the invention allow acting as thermo-thickening agent while ensuring efficient mechanical engine operation both at low and high temperatures.

Advantageously, the compounds or composition of the invention allow to slow down the evaporation of a non-polar liquid, especially a perfume.

Kit

The present invention also relates to a kit comprising in one compartment a compound of the invention as defined above, and in a second compartment a non-polar liquid as defined above.

EXAMPLES

Figure 1:
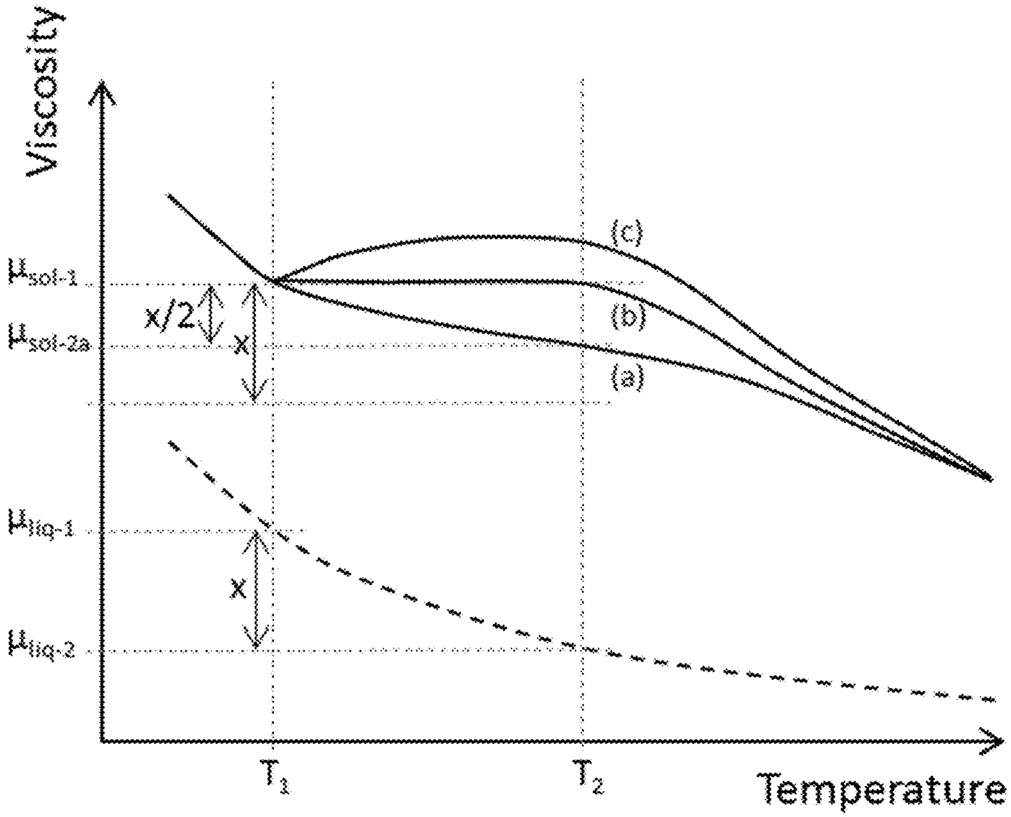
FIG. 1 is a theoretical graph of the variation of the viscosity in function of the temperature for a liquid (dotted line) and for the same liquid comprising a thermo-thickening compound of the invention (solid line).

The present invention is further illustrated by the following examples.

Part 1: Chemistry

Abbreviations

Ala Alanine;
AcOEt Ethyl acetate;
Ar Aromatic group;
$CDCl_3$ Chloroform;
DCM Dichloromethane;
DIEA N,N-Diisopropylethylamine;
DIPA Diisopropylamine;
DMSO Dimethylsulfoxyde;
ESI Electrospray Ionization;
eq. Equivalent;
HMPA Hexamethylphosphoramide;
HRMS High-resolution mass spectrometry;
LDA Lithium diisopropylamide;
Leu et i-Leu Leucine and iso-Leucine;
M Molar;
min Minute(s);
MS Mass spectrometry;
NMR Nuclear magnetic resonance;
PE Petroleum ether;
Phe Phenylalanine;
PhGly Phenylglycine;
PTSA p-Toluenesulfonic acid;
TDI Toluene diisocyanate;
THF Tetrahydrofurane;
THP Tetrahydropyrane.

Materials and Methods

All amino acids were purchased from Sigma-Aldrich or Alfa Aesar (99% purity) and used as received. TDI was purchased from Sigma Aldrich (purity≥98%) and was used directly. Chromatography-grade solvents were used as received. Dried $CH_2Cl_2$ and THF were obtained from an SPS solvent purification system (IT-Inc) and stored on 4 Å molecular sieves. $NEt_3$ and DIEA were dried by distillation over CaH2 and stored over 4 Å molecular sieves.

NMR Spectroscopy

NMR spectra were recorded on a Bruker Avance 400, 300 or 200 spectrometers and calibrated to the residual solvent peak. Peaks are reported in ppm with their corresponding multiplicity (s: singlet; d: doublet, t: triplet; q: quartet; quint: quintet; hept: heptuplet; dt: doublet of triplets; td: triplet of doublets), integration, and respective J coupling constants are given in hertz.

HRMS Spectrometer

Exact mass measurements (HRMS) were obtained on TQ R30-10 HRMS spectrometer by ESI+ ionization and are reported in m/z for the major signal.

Flash Chromatography

The flash chromatography purification was made with a Grace Reveleris and columns of the same brand. The water was purified using a milli-Q system.

Fourier Transform InfraRed Spectroscopy (FT-IR)

FT-IR measurements were performed on a Nicolet iS10 spectrometer in a CaF2 cell of 1.0 mm pathlength and are corrected for air, solvent and cell absorption.

Rheology Measurements

Rheology measurements were performed on a Haake RS600 rheometer equipped with a sandblasted stainless steel cone/plate geometry with a 35 mm diameter, a 53 μm gap and a 2° angle. The temperature is controlled with a Peltier thermostat.

Viscosimetry Measurements

Viscosimetry measurements were recorded using an Anton paar AMVn falling-ball microviscometer with a 0.16 mm diameter capillary, with three measurements at an angle of +20° and −20°. Results are reported as an average of those six measurements.

Example 1

General Procedures for Preparing Ester Bis-Ureas 1.1. Synthesis of Ester Ammonium Tosylate Salts (Preliminary Step)

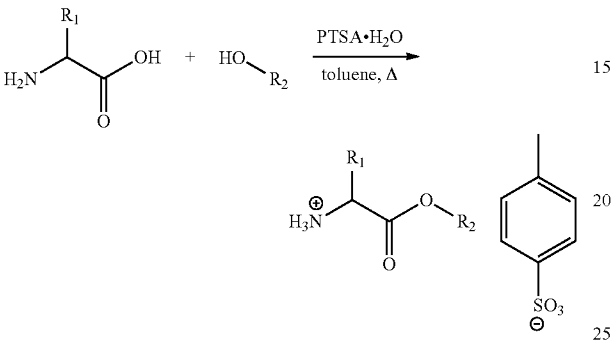

This synthesis was adapted from: S. Cantekin, H. M. M. ten Eikelder, A. J. Markvoort, M. A. J. Veld, P. A. Korevaar, M. M. Green; A. R. A. Palmans, E. W. Meijer, *Angew. Chem. Int. Ed.* 2012, 51, 6426-6431.

1 eq. of amino acid, 1.1 eq. of alcohol and 1.1 eq. of PTSA.$H_2O$ were added to toluene (0.15M) and the mixture was stirred under reflux equipped with a Dean-Stark apparatus for 12 h. The mixture was then concentrated under reduced pressure and diluted in $Et_2O$. The solution was put into ice to precipitate for a couple of hours. The precipitate was then filtered, washed with cold $Et_2O$ and dried under vacuum.

1.2. Synthesis of Ester Bis-Ureas with a Toluene Spacer (Method A)

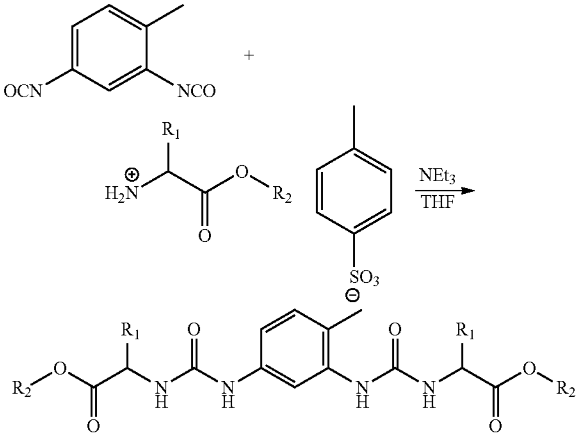

This synthesis was adapted from: F. Lortie, S. Boileau, L. Bouteiller, C. Chassenieux, B. Demé, G. Ducouret, M. Jalabert, F. Laupretre, P. Terech, *Langmuir* 2002, 18, 7218-7222.

2.2 eq. of the ammonium ester tosylate (obtained according to method as defined above) was dissolved in anhydrous THF (0.05 M) under argon. 2.2 eq. of $NEt_3$ and 1 eq. of TDI were added to the mixture. The mixture was stirred at room temperature for 48 h. The mixture was then concentrated under reduced pressure and either purified by column chromatography or recrystallized from acetonitrile.

1.3. Synthesis of Ester Bis-Ureas with Other Spacers (Method B)

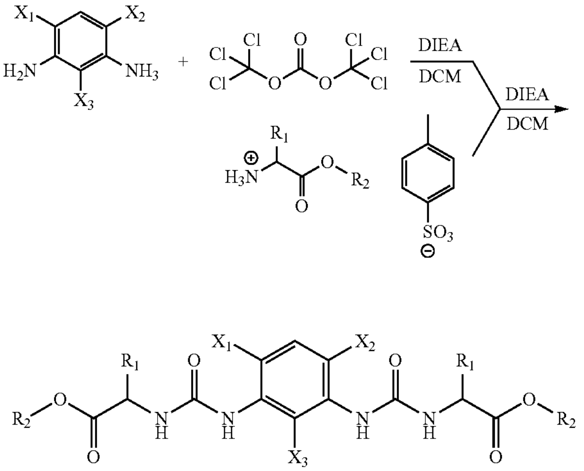

This synthesis was adapted from: I. Giannicchi, B. Jouvelet, B. Isare, M. Linares, A. Dalla Cort, L. Bouteiller, *Chem. Commun.* 2014, 50, 611-613.

Under argon atmosphere, a 70 mM solution of the diaminobenzene derivative and 2 eq. of DIEA in DCM was added at 2.5 mL/h to a 60 mM solution of 0.66 eq. of triphosgene in DCM. The mixture was stirred for 1 h after addition and a 0.3 M solution of 2.1 eq. of the ammonium ester tosylate and 6.3 eq. of DIEA in DCM was added to the mixture. The solution was concentrated under reduced pressure and the product was either purified by column chromatography or recrystallized from acetonitrile.

Example 2

Synthesis of Ester Ammonium Tosylate Salts 2.2. Linear Compounds 2.2.1. Synthesized from Phenylalanine Hexyl (S)-Phenylalaninate Ammonium Tosylate Salt

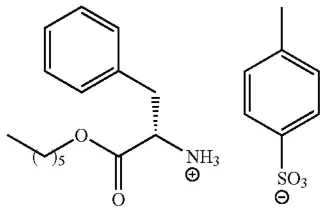

Preparation was achieved following the preliminary step as described above, using commercially available hexanol and (S)-Phenylalanine. The product was obtained as a white powder.

Heptyl (S)-Phenylalaninate Ammonium Tosylate Salt

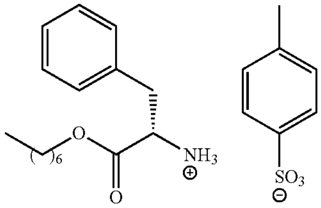

Preparation was achieved following the preliminary step as described above, using commercially available heptanol and (S)-Phenylalanine. 3.41 g (99%) of product were obtained as a white powder.

$^{1}$H NMR (400 MHz, $CDCl_3$) δ 8.24 (s, 3H, NH3), 7.74 (d, 2H, Ar—H, J=7.8 Hz), 7.20-7.03 (m, 7H, Ar—H), 4.31-4.18 (m, 1H, NH3-CH), 3.94-3.77 (m, 2H, COO—CH2), 3.24 (dd, 1H, NH3-CH—CH2, J=14.0, 5.3 Hz), 3.04 (dd, NH3-CH—CH2, 1H, J=14.0, 8.2 Hz), 2.32 (s, 3H, Ar—CH3), 1.37-1.07 (m, 12H, CH2), 1.07-0.97 (m, 2H, CH2), 0.88 (t, 3H, CH3, J=6.5 Hz). $^{13}$C NMR (101 MHz, $CDCl_3$) δ 169.02, 141.70, 140.33, 134.48, 129.57, 128.92, 128.69, 127.34, 126.34, 54.34, 36.53, 32.07, 29.86, 29.80, 29.65, 29.50, 29.37, 28.23, 25.75, 22.83, 21.45, 14.25.

Octyl (S)-Phenylalaninate Ammonium Tosylate Salt

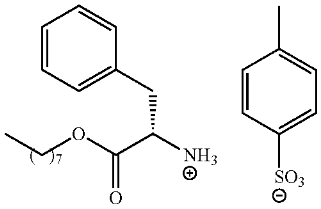

Preparation was achieved following the preliminary step as described above, using commercially available octanol and (S)-Phenylalanine. 5.94 g (95%) of product were obtained as a white powder.

$^{1}$H NMR (300 MHz, $CDCl_3$) δ 8.44 (s, 3H, NH3), 7.50 (d, 2H, Ar—H, 2J=7.6 Hz), 7.38-7.02 (m, 7H, Ar—H), 4.25 (t, 1H, NH3-CH, $^{2}$J=6.6 Hz), 3.99 (t, 2H, COO—CH2, $^{2}$J=6.3 Hz), 3.08 (AB spin sytem, 2H, NH3-CH—CH2, $^{2}$J=8.1 Hz), 1.80 (quin, 2H, COO—CH2-CH2, $^{2}$J=1.8 Hz), 2.27 (s, 3H, Ar—CH3), 1.39 (quin, 2H, COO—CH2-CH2-CH2, $^{2}$J=6.5 Hz), 1.30-1.00 (m, 10H, CH2), 0.85 (t, 3H, CH3, $^{2}$J=7.0 Hz). $^{13}$C NMR (101 MHz, $CDCl_3$) δ 169.01, 141.69, 140.33, 134.49, 129.56, 128.91, 128.67, 127.33, 126.33, 66.37, 54.33, 31.93, 29.28, 29.25, 28.21, 25.72, 22.77, 21.44, 14.22.

Nonyl (S)-Phenylalaninate Ammonium Tosylate Salt

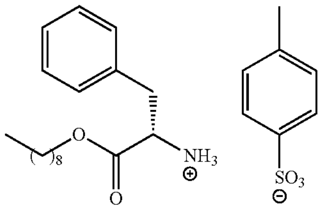

Preparation was achieved following the preliminary step as defined above, using commercially available nonanol and (S)-Phenylalanine. 5.32 g (91%) of product were obtained as a white powder.

$^{1}$H NMR (300 MHz, $CDCl_3$) δ 8.24 (s, 3H, NH3), 7.75 (d, 2H, Ar—H, $^{2}$J=8.1 Hz), 7.19-7.03 (m, 7H, Ar—H), 4.30-4.20 (m, 1H, NH3-CH), 3.95-3.80 (m, 2H, COO—CH2), 3.15 (AB spin sytem, 2H, NH3-CH—CH2), 2.33 (s, 3H, Ar—CH3), 1.39-1.00 (m, 14H, CH2), 0.90 (t, 3H, CH3, $^{2}$J=7.0 Hz)$^{13}$C NMR (101 MHz, $CDCl_3$) δ 168.86, 141.53, 140.23, 134.32, 129.44, 128.79, 128.56, 127.22, 126.21, 66.26, 54.20, 36.39, 31.87, 29.44, 29.28, 29.21, 28.10, 25.60, 22.67, 21.31, 14.11.

Decyl (S)-Phenylalaninate Ammonium Tosylate Salt

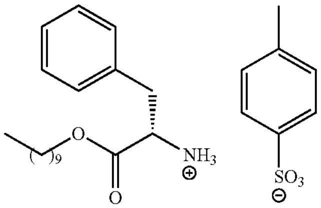

Preparation was achieved following the preliminary step as defined above, using commercially available decanol and (S)-Phenylalanine. 3.22 g (59%) of product were obtained as a white powder.

$^{1}$H NMR (300 MHz, $CDCl_3$) δ 8.24 (s, 3H, NH3), 7.75 (d, 2H, Ar—H, $^{2}$J=8.1 Hz), 7.19-7.03 (m, 7H, Ar—H), 4.30-4.20 (m, 1H, NH3-CH), 3.95-3.80 (m, 2H, COO—CH2), 3.15 (AB spin sytem, 2H, NH3-CH—CH2), 2.33 (s, 3H, Ar—CH3), 1.39-1.00 (m, 16H, CH2), 0.90 (t, 3H, CH3, $^{2}$J=7.0 Hz; $^{13}$C NMR (101 MHz, $CDCl_3$) δ 169.01, 141.67, 140.36, 134.47, 129.57, 128.92, 128.69, 127.35, 126.34, 66.39, 54.34, 36.53, 32.04, 29.71, 29.62, 29.46, 29.35, 28.23, 25.74, 22.82, 21.45, 14.25.

Undecyl (S)-Phenylalaninate Ammonium Tosylate Salt

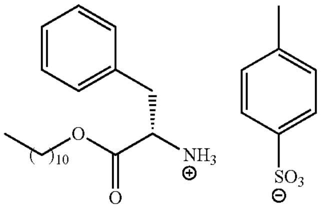

Preparation was achieved following the preliminary step as defined above, using commercially available undecanol and (S)-Phenylalanine. 2.13 g (82%) of product were obtained as a white powder.

$^{1}$H NMR (300 MHz, $CDCl_3$) δ 8.24 (s, 3H, NH3), 7.75 (d, 2H, Ar—H, $^{2}$J=8.1 Hz), 7.19-7.03 (m, 7H, Ar—H), 4.30-4.20 (m, 1H, NH3-CH), 3.95-3.80 (m, 2H, COO—CH2), 3.15 (AB spin sytem, 2H, NH3-CH—CH2), 2.33 (s, 3H, Ar—CH3), 1.39-1.00 (m, 18H, CH2), 0.90 (t, 3H, CH3, $^{2}$J=7.0 Hz). $^{13}$C NMR (101 MHz, $CDCl_3$) δ 169.01, 141.70, 140.33, 134.49, 129.57, 128.92, 128.67, 127.33, 126.34, 66.38, 54.34, 36.53, 32.06, 29.82, 29.79, 29.77, 29.63, 29.50, 29.36, 25.74, 22.83, 21.44, 14.25.

Dodecyl (S)-Phenylalaninate Ammonium Tosylate Salt

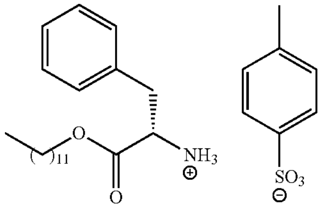

Preparation was achieved following the preliminary step as defined above, using commercially available dodecanol and (S)-Phelylalanine 10.62 g (86%) of product were obtained as a white powder.

$^1$H NMR (400 MHz, $CDCl_3$) δ 8.24 (s, 3H, NH3), 7.74 (d, 2H, Ar—H, J=8.2 Hz), 7.20-7.04 (m, 6H, Ar—H), 4.29-4.19 (m, 1H, NH3-CH), 3.93-3.77 (m, 2H, COO—CH2), 3.24 (dd, 1H, NH3-CH—CH2, J=14.0, 5.3 Hz), 3.04 (dd, 1H, NH3-CH—CH2, J=14.0, 8.4 Hz), 2.32 (s, 3H, Ar—CH3), 1.38-1.08 (m, 14H, CH2), 1.08-0.96 (m, 2H, CH2), 0.89 (t, 3H CH3, J=6.8 Hz). $^{13}$C NMR (101 MHz, $CDCl_3$) δ 169.02, 141.70, 140.31, 134.52, 129.56, 128.90, 128.65, 127.30, 126.33, 66.35, 54.34, 36.53, 32.05, 29.81, 29.78, 29.76, 29.62, 29.49, 29.35, 28.21, 25.73, 22.81, 21.43, 14.24.

Dodecyl (R)-Phenylalaninate Ammonium Tosylate Salt

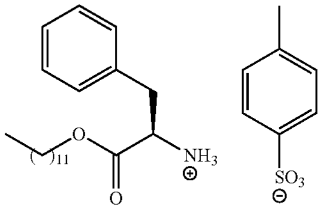

Preparation was achieved following the preliminary step as defined above, using commercially available dodecanol and (R)-Phenylalanine. 2.12 g (86%) of product were obtained as a white powder.

$^1$H NMR (300 MHz, $CDCl_3$) δ 8.21 (s, 3H, NH3), 7.72 (d, 2H, Ar—H, $^2$J=8.1 Hz), 7.18-7.03 (m, 7H, Ar—H), 4.30-4.16 (m, 1H, NH3-CH), 3.94-3.76 (m, 2H, COO—CH2), 3.14 (AB spin sytem, 2H, NH3-CH—CH2), 2.31 (s, 3H, Ar—CH3), 1.40-0.97 (m, 28H, CH2), 0.87 (t, 2H, CH3, $^2$J=7.0 Hz). $^{13}$C NMR (101 MHz, $CDCl_3$) δ 169.02, 141.70, 140.32, 134.52, 129.56, 128.91, 128.66, 127.31, 126.34, 66.36, 54.34, 36.53, 32.05, 29.76, 29.63, 29.49, 29.35, 28.22, 25.73, 22.82, 21.43, 14.24.

Tridecyl (S)-Phenylalaninate Ammonium Tosylate Salt

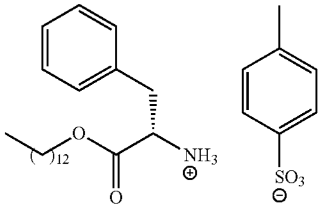

Preparation was achieved following the preliminary step as defined above, using commercially available decanol and (S)-Phenylalanine. 4.14 g (88%) of product were obtained as a white powder.

$^1$H NMR (400 MHz, $CDCl_3$) δ 8.18 (s, 3H, NH3), 7.76 (d, 2H, Ar—H, J=7.9 Hz), 7.23-7.05 (m, Ar—H, 7H), 4.27 (dd, NH3-CH, 1H, J=8.1, 5.3 Hz), 3.88 (m, 2H, COO—CH2), 3.27 (dd, 1H, NH3-CH—CH2, J=14.1, 5.3 Hz), 3.07 (dd, 1H, NH3-CH—CH2, J=14.1, 8.2 Hz), 2.35 (s, 3H, Ar—CH3), 1.43-1.11 (m, 20H, CH2), 1.06 (q, 2H, CH2, J=7.7 Hz), 0.91 (t, 3H, CH3, J=6.6 Hz). $^{13}$C NMR (101 MHz, $CDCl_3$) δ 141.69, 140.35, 134.45, 129.57, 128.93, 128.70, 127.36, 126.32, 66.40, 54.34, 29.84, 29.82, 29.80, 29.77, 29.63, 29.50, 29.36, 28.23, 25.75, 22.83, 21.45, 14.25.

Tetradecyl (S)-Phenylalaninate Ammonium Tosylate Salt

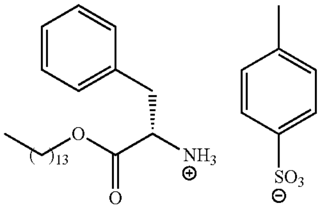

Preparation was achieved following the preliminary step as defined above, using commercially available decanol and (S)-Phenylalanine. 1.47 g (33%) of product were obtained as a white powder.

$^1$H NMR (400 MHz, $CDCl_3$) δ 8.24 (s, 3H, NH3), 7.74 (d, 2H, Ar—H, J=8.0 Hz), 7.21-7.02 (m, 7H, Ar—H), 4.24 (dd, 1H, NH3-CH, J=8.2, 5.3 Hz), 3.95-3.76 (m, 2H, COO—CH2), 3.24 (dd, 1H, NH3-CH—CH2, J=14.1, 5.3 Hz), 3.05 (dd, 1H, NH3-CH—CH2, J=14.0, 8.2 Hz), 2.33 (s, 3H, Ar—CH3), 1.45-1.09 (m, 21H, CH2), 1.04 (q, 2H, CH2, J=7.7 Hz), 0.89 (t, 3H, CH3, J=6.7 Hz). $^{13}$C NMR (101 MHz, $CDCl_3$) δ 141.70, 140.35, 134.45, 129.58, 128.93, 128.70, 127.36, 126.33, 66.40, 54.33, 29.85, 29.83, 29.81, 29.78, 29.64, 29.51, 29.37, 28.24, 25.75, 22.83, 21.45, 14.25.

Hexadecyl (S)-Phenylalaninate Ammonium Tosylate Salt

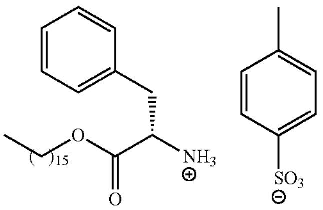

Preparation was achieved following the preliminary step as defined above, using commercially available decanol and (S)-Phenylalanine. 5.84 g (92%) of product were obtained as a white powder.

$^1$H NMR (300 MHz, $CDCl_3$) δ 8.21 (s, 3H, NH3), 7.72 (d, 2H, Ar—H, $^2$J=8.2 Hz), 7.16-7.034 (m, 7H, Ar—H), 4.27-4.17 (m, 1H, NH3-CH), 3.91-3.77 (m, 2H, COO—CH2), 3.12 (AB spin sytem, 2H, NH3-CH—CH2), 2.31 (s, 3H, Ar—CH3), 1.35-1.06 (m, 28H, CH2), 0.86 (t, 3H, CH3, $^2$J=7.0 Hz). $^{13}$C NMR (101 MHz, $CDCl_3$) δ 168.88, 141.56, 140.21, 134.34, 129.44, 128.79, 128.56, 127.22, 126.21, 66.26, 54.21, 36.40, 31.94, 29.73, 29.71, 29.68, 29.66, 29.52, 29.37, 29.24, 28.11, 25.62, 22.70, 21.32, 14.12.

Octadecyl (S)-Phenylalaninate Ammonium Tosylate Salt

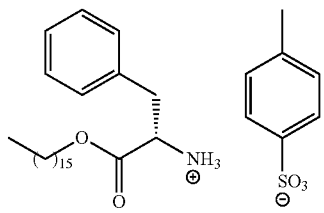

Preparation was achieved following the preliminary step as defined above, using commercially available 1-octadecanol and (S)-Phenylalanine. The product is obtained as a white powder.

2.2.2. Synthesized from Other Aminoacids

Octyl (S)-$d_5$-Phenylalaninate Ammonium Tosylate Salt

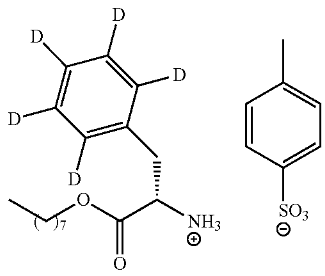

Preparation was achieved following the preliminary step as defined above, using commercially available octanol and (S)-$d_5$-Phenylalanine. 2.32 g (85%) of product were obtained as a white powder.

$^1$H NMR (300 MHz, DMSO-$d_6$) δ 8.45 (s, 3H, NH3), 7.23 (d, 2H, Ar—H, $^2$J=8.1 Hz), 6.84 (d, 2H, Ar—H, $^2$J=8.0 Hz), 4.28 (t, 1H, NH3-CH, $^2$J=6.9 Hz), 4.02 (t, 2H, COO—CH2, $^2$J=6.4 Hz), 3.10 (AB system, 2H, NH3-CHCH2), 2.29 (s, 3H, Ar—CH3), 1.48-1.34 (m., 2H, COO—CH2CH2), 1.34-1.06 (m, 10H, CH2), 0.87 (t, 12H, CH3, $^2$J=6.8 Hz) $^{13}$C NMR (75 MHz, DMSO-$d_6$) δ 127.81, 125.22, 65.27, 52.98, 35.78, 30.91, 28.23, 27.49, 24.82, 21.79, 20.48, 13.64.

2.2.3. Halogen-Functionalized Compounds

12-Tribromododecyl (S)-Phenylalaninate Ammonium Tosylate Salt

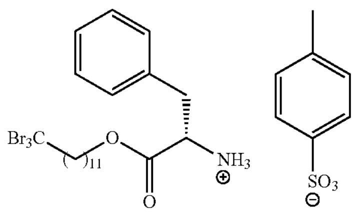

Preparation was achieved following the preliminary step as defined above, using 12-tribromododecanol and (S)-phenylalanine. 6.57 g (85%) of product were obtained as a white powder.

$^1$H NMR (300 MHz, $CDCl_3$) δ 8.41 (s, 3H, NH3), 7.50 (d, 2H, Ar—H, $^2$J=8.0 Hz), 7.32 (q, 3H, Ar—H, $^2$J=7.3 Hz), 7.22 (d, 2H, Ar—H, $^2$J=7.1 Hz), 7.12 (d, 2H, Ar—H, $^2$J=7.9 Hz), 4.29 (t, 1H, NH3-CH, $^2$J=6.9 Hz), 4.02 (t, 2H, COO—CH2, $^2$J=6.4 Hz), 3.09 (AB spin sytem, 2H, NH3-CH—CH2, $^2$J=21.7 Hz), 2.96 (t, 2H, CBr3-CH2, $^2$J=7.8 Hz), 2.29 (s, 3H, Ar—CH3), 1.68 (quin, 2H, COO—CH2-CH2, $^2$J=7.4 Hz), 1.50-1.08 (m, 16H, CH2). $^{13}$C NMR (101 MHz, $CDCl_3$) δ 169.02, 141.64, 140.35, 134.43, 129.56, 128.92, 128.70, 127.37, 126.30, 66.37, 60.06, 54.33, 42.77, 36.51, 29.65, 29.57, 29.45, 29.31, 28.21, 28.01, 25.72, 21.48. HRMS (ESI, m/z) 570.0044 [M]$^+$, 570.0035 calculated for $C_{21}H_{33}Br_3NO_2$.

12-Trichlorododecyl (S)-Phenylalaninate Ammonium Tosylate Salt

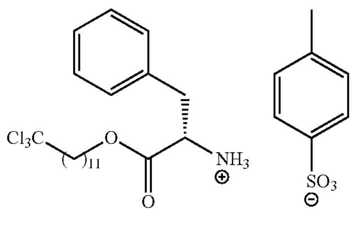

Preparation was achieved following the preliminary step as defined above, using 12-trichlorododecanol and (S)-phenylalanine. 617 mg (76%) of product were obtained as a white powder.

$^1$H NMR (300 MHz, $CDCl_3$) δ 8.22 (s, 3H, NH3), 7.74 (d, 2H, Ar—H, $^2$J=8.2 Hz), 7.21-7.07 (m, 7H, Ar—H), 4.35-4.20 (m, 1H, NH3-CH), 3.98-3.82 (m, 2H, COO—CH2), 3.17 (AB spin sytem, 2H, NH3-CH—CH2, $^2$J=5.9 Hz), 2.67 (t, 2H, CC13-CH2, $^2$J=8.0 Hz), 2.34 (s, 3H, Ar—CH3), 1.78 (quin, 2H, COO—CH2-CH2, $^2$J=7.4 Hz), 1.48-1.00 (m, 16H, CH2). $^{13}$C NMR (101 MHz, $CDCl_3$) δ 169.00, 141.62, 140.40, 134.46, 129.57, 128.94, 128.70, 127.37, 126.32, 66.37, 55.34, 54.35, 36.53, 29.65, 29.56, 29.44, 29.32, 28.48, 28.22, 26.53, 25.73, 21.47. HRMS (ESI, m/z) 436.1575 [M]$^+$, 436.1571 calculated for $C_{21}H_{33}Cl_3NO_2$.

Example 3

Symmetric Ester Bis-Ureas with Linear Alkyl Chains 3.1. Bis-Ureas Synthetized from Phenylalanine (Phe)

H3C5Tol

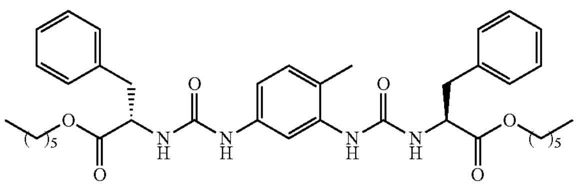

Preparation was achieved following the method A using hexyl (S)-phenylalaninate ammonium tosylate salt. The product is recrystallized in acetonitrile. 726 mg (85%) of a pure product were obtained as a white paste.

$^1$H NMR (400 MHz, DMSO-$d_6$) δ 8.60 (s, 1H, NH), 7.81 (s, 1H, NH), 7.73 (d, 1H, ArH, J=2.2 Hz), 7.35-7.17 (m, 11H, ArH), 7.11 (dd, 1H, ArH, J=8.2, 2.2 Hz), 6.94 (d, 2H, NH, J=8.0 Hz), 6.28 (d, 1H, ArH, J=7.9 Hz), 4.58-4.45 (m, 2H, NH—CH), 4.02 (t, 4H, COO—CH2, J=6.5 Hz), 3.09-2.93 (m, 4H, NH3-CH—CH2), 2.08 (s, 3H, Ar—CH3), 1.58-1.45 (m, 4H, CH2), 1.31-1.17 (m, 13H, CH2), 0.84 (t, 6H, CH3, J=6.8 Hz). $^{13}$C NMR (101 MHz, DMSO-$d_6$) δ

172.20, 154.63, 154.48, 138.10, 137.80, 136.85, 136.78, 129.94, 129.13, 128.26, 126.58, 119.48, 111.64, 110.01, 64.46, 53.97, 53.73, 37.72, 37.56, 30.83, 27.99, 24.95, 21.94, 17.18, 13.82.

H3C6Tol

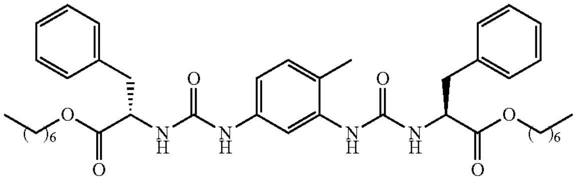

Preparation was achieved following the method A using heptyl (S)-phenylalaninate ammonium tosylate salt. The product is recrystallized in acetonitrile. 823 mg (88%) of a pure product were obtained as a white paste.

$^1$H NMR (400 MHz, DMSO-$d_6$/THF-$d_8$ 2/1) δ 8.60 (s, 1H, NH), 7.81 (s, 1H, NH), 7.77 (s, 1H, ArH), 7.34-7.15 (m, 13H, ArH), 6.96 (d, 1H, NH, J=7.8 Hz), 6.90 (d, 1H, NH, J=8.3 Hz), 6.28 (d, 1H, ArH, J=8.0 Hz), 4.57 (h, 2H, NH—CH, J=7.0 Hz), 4.04 (t, 4H, COO—CH2, J=6.7 Hz), 3.12-2.92 (m, 4H, NH3-CH—CH2), 2.11 (s, 3H, Ar—CH3), 1.62-1.48 (m, 4H, CH2), 1.26 (s, 16H, CH2), 0.87 (t, 6H, CH3, J=6.5 Hz). $^{13}$C NMR (101 MHz, DMSO-$d_6$/THF-$d_8$ 2/1) δ 172.10, 154.58, 154.44, 138.39, 137.97, 136.96, 129.65, 129.10, 128.06, 126.37, 118.98, 114.60, 111.35, 109.69, 64.36, 53.95, 53.72, 38.04, 37.87, 31.43, 25.45, 22.18, 17.03, 13.58. HRMS (ESI, m/z) 723.4100 [M+Na]$^+$, 723.4092 calculated for $C_{46}H_{56}N_4O_6Na$.

H3C7Tol

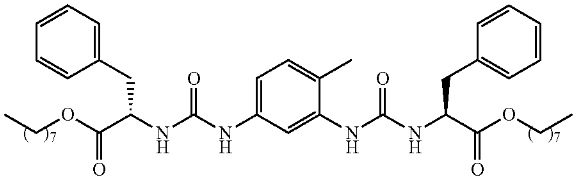

Preparation was achieved following the method A using heptyl (S)-phenylalaninate ammonium tosylate salt. The product is recrystallized in acetonitrile.

HRMS (ESI, m/z) 751.4405 [M+Na]$^+$, 751.4405 calculated for $C_{43}H_{60}N_4O_6Na$ H3C7Xyl

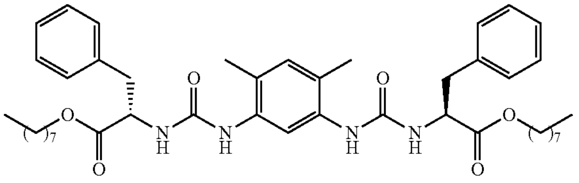

Preparation was achieved following the method B using octyl (S)-phenylalaninate ammonium tosylate salt and 4,6-dimethyl-1,3-diaminobenzen. The product is recrystallized in acetonitrile. 963 mg (61%) of a pure product were obtained as a white paste.

$^1$H NMR (300 MHz, DMSO-$d_6$) δ 7.94 (s, 1H, ArH), 7.75 (s, 2H, NH), 7.36-7.15 (m, 10H, ArH and NH), 6.85 (s, 1H, ArH), 6.69 (d, 2H, ArH, $^2$J=7.9 Hz), 4.49 (q, 2H, NH—CH, $^2$J=7.2 Hz), 4.00 (t, 4H, COO—CH2, $^2$J=6.5 Hz), 3.08-2.91 (m, NH3-CH—CH2, 4H), 2.05 (s, 6H, Ar—CH3), 1.50 (q, 4H, COOCHC2CH2, $^2$J=6.0 Hz), 1.30-1.15 (m, 20H, CH2), 0.85 (t, 6H, CH3, $^2$J=6.7 Hz). $^{13}$C NMR (101 MHz, DMSO-$d_6$) δ 172.27, 154.73, 136.87, 135.27, 131.20, 129.12, 128.22, 126.53, 122.40, 115.64, 64.42, 53.91, 37.74, 31.20, 28.59, 28.54, 28.01, 25.27, 22.06, 17.17, 13.90. HRMS (ESI, m/z) 765.4570 [M+Na]$^+$, 765.4562 calculated for $C_{44}H_{62}N_4O_6Na$.

H3C7Cl

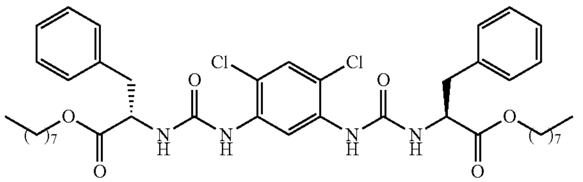

Preparation was achieved following the method B using octyl (S)-phenylalaninate ammonium tosylate salt and 4,6-dichloro-1,3-diaminobenzene. The product is recrystallized in acetonitrile. 457 mg (55%) of pure product were obtained as a white powder.

$^1$H NMR (400 MHz, DMSO-$d_6$) δ 8.91 (s, 1H, ArH), 8.21 (s, 2H, NH), 7.46 (s, 1H, ArH), 7.41 (d, 2H, J=7.7 Hz, ArH), 7.34-7.17 (m, 12H, ArH and NH), 4.49 (q, 2H, NH—CH, J=7.7 Hz), 4.01 (t, 4H, COO—CH2, J=6.2 Hz), 3.08-2.91 (m, 4H NH3-CH—CH2), 1.55-1.42 (m, 4H, CH2), 1.30-1.13 (m, 20H, CH2), 0.83 (t, 6H, CH3, J=6.8 Hz). $^{13}$C NMR (101 MHz, DMSO-$d_6$) δ 172.00, 153.90, 136.74, 135.43, 129.07, 128.28, 126.61, 114.37, 112.83, 64.52, 54.01, 37.48, 31.19, 28.59, 28.55, 28.00, 25.28, 22.06, 13.89. HRMS (ESI, m/z) 805.3468 [M+Na]$^+$, 805.3469 calculated for $C_{42}H_{56}Br_4Cl_2N_4O_6Na$.

H3C8Tol

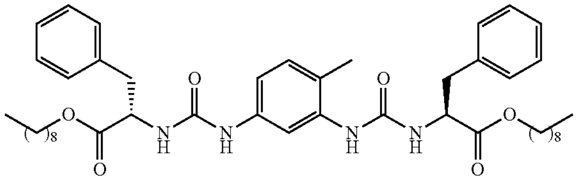

Preparation was achieved following the method A using nonyl (S)-phenylalaninate ammonium tosylate salt. The product is recrystallized in acetonitrile. 1.42 g (83%) of a pure product were obtained as a white paste.

$^1$H NMR (300 MHz, DMSO-$d_6$) δ 8.58 (s, 1H, ArH), 7.75 (d, 2H, NH, $^2$J=30.5 Hz), 7.35-7.15 (m, 10H, ArH), 7.10 (d, 1H, NH, $^2$J=8.3 Hz), 6.92 (d, 2H, ArH, $^2$J=7.9 Hz), 6.26 (d, 1H, NH, $^2$J=7.9 Hz), 4.49 (p, 2H, NH—CH, $^2$J=7.3 Hz), 4.01 (t, 4H, COO—CH2, $^2$J=6.4 Hz), 3.06-2.92 (m, 4H, NH3-CH—CH2), 2.07 (s, 3H, Ar—CH3), 1.55-1.44 (m, 4H, COO—CH2-CH2), 1.30-1.15 (m, 24H, CH2), 0.85 (t, 3H, CH3, $^2$J=6.9 Hz). $^{13}$C NMR (101 MHz, DMSO-$d_6$) δ 172.18, 154.61, 154.46, 138.07, 137.78, 136.84, 136.78, 129.93, 129.11, 128.25, 126.57, 119.41, 111.58, 109.94, 64.44, 53.96, 53.73, 37.68, 37.52, 31.24, 28.84, 28.62, 28.01, 25.27, 22.06, 17.18, 13.91. HRMS (ESI, m/z) 779.4716 [M+Na]$^+$, 779.4718 calculated for $C_{45}H_{64}N_4O_6Na$.

H3C8Xyl

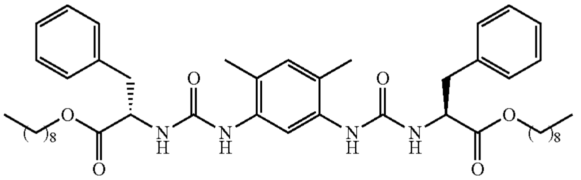

Preparation was achieved following the method B using nonyl (S)-phenylalaninate ammonium tosylate salt and 4,6-dimethyl-1,3-diaminobenzene. The product is recrystallized in acetonitrile. 465 mg (59%) of a pure product were obtained as a white paste.

$^1$H NMR (300 MHz, DMSO-$d_6$) δ 7.94 (s, 1H, ArH), 7.75 (s, 2H, NH), 7.36-7.15 (m, 10H, ArH and NH), 6.85 (s, 1H, ArH), 6.69 (d, 2H, ArH, $^2$J=7.9 Hz), 4.49 (q, 2H, NH—CH, $^2$J=7.2 Hz), 4.00 (t, 4H, COO—CH2, $^2$J=6.5 Hz), 3.08-2.91 (m, NH3-CH—CH2, 4H), 2.05 (s, 6H, Ar—CH3), 1.50 (q, 4H, COOCHC2CH2, $^2$J=6.0 Hz), 1.30-1.15 (m, 24H, CH2), 0.85 (t, 6H, COO—CH2, $^2$J=6.7 Hz). $^{13}$C NMR (101 MHz, DMSO-$d_6$) δ 172.27, 154.73, 136.87, 135.26, 131.19, 129.11, 128.22, 126.52, 122.38, 64.41, 53.90, 37.73, 31.25, 28.62, 28.00, 25.26, 22.07, 17.17, 13.91. HRMS (ESI, m/z) 793.4886 [M+Na]$^+$, 793.4875 calculated for $C_{46}H_{66}N_4O_6Na$.

H3C9Tol

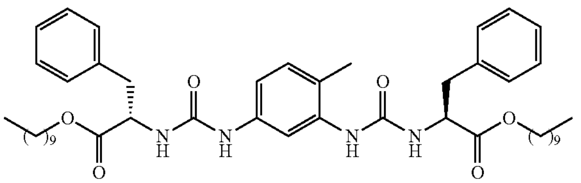

Preparation was achieved following the method A using decyl (S)-phenylalaninate ammonium tosylate salt. The product is recrystallized in acetonitrile. 1.42 g (83%) of a pure product were obtained as a white paste.

$^1$H NMR (400 MHz, DMSO-$d_6$) δ 8.60 (s, 1H, ArH), 7.78 (d, 2H, NH, $^2$J=28.8 Hz), 7.42-7.12 (m, 10H, ArH), 7.12 (d, 1H, NH, $^2$J=6.9 Hz), 6.94 (d, 2H, ArH, $^2$J=5.1 Hz), 6.28 (d, 1H, NH, $^2$J=6.7 Hz), 4.59-4.44 (m, 2H, NH—CH), 4.02 (t, 4H, COO—CH2, $^2$J=6.4 Hz), 3.06-2.92 (m, 4H, NH3-CH—CH2), 2.09 (s, 3H, Ar—CH3), 1.58-1.45 (m, 4H, COO—CH2-CH2), 1.30-1.15 (m, 28H, CH2), 0.86 (t, 3H, CH3, $^2$J=6.9 Hz). $^{13}$C NMR (101 MHz, DMSO-$d_6$) δ 172.17, 154.61, 154.46, 138.09, 137.79, 136.84, 136.78, 129.91, 129.11, 128.23, 126.55, 119.38, 111.58, 109.94, 64.44, 53.96, 53.73, 37.71, 37.55, 31.28, 28.93, 28.92, 28.90, 28.69, 28.64, 28.02, 25.28, 22.09, 17.18, 13.90. HRMS (ESI, m/z) 807.5029 [M+Na]$^+$, 807.5031 calculated for $C_{47}H_{88}N_4O_6Na$.

H3C10Tol

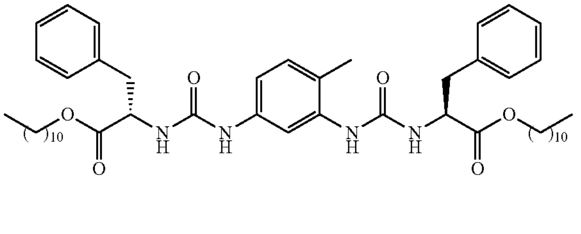

Preparation was achieved following the method A using undecyl (S)-phenylalaninate ammonium tosylate salt. The product is recrystallized in acetonitrile. 1.82 g (99%) of a pure product were obtained as a white paste.

$^1$H NMR (400 MHz, DMSO-$d_6$) δ 8.60 (s, 1H, ArH), 7.78 (d, 2H, NH, $^2$J=27.5 Hz), 7.37-7.14 (m, 10H, ArH), 7.12 (d, 1H, NH, $^2$J=6.7 Hz), 6.94 (d, 2H, ArH, $^2$J=5.1 Hz), 6.28 (d, 1H, NH, $^2$J=6.0 Hz), 4.59-4.44 (m, 2H, NH—CH), 4.02 (t, 4H, COO—CH2, $^2$J=6.4 Hz), 3.06-2.92 (m, 4H, NH3-CH—CH2), 2.09 (s, 3H, Ar—CH3), 1.58-1.45 (m, 4H, COO—CH2-CH2), 1.30-1.15 (m, 32H, CH2), 0.86 (t, 3H, CH3, $^2$J=6.9 Hz). $^{13}$C NMR (101 MHz, DMSO-$d_6$) δ 172.16, 154.45, 138.10, 137.79, 136.84, 136.77, 129.90, 129.10, 128.22, 126.54, 119.36, 111.58, 109.94, 64.43, 53.95, 53.72, 37.71, 37.56, 31.29, 28.99, 28.90, 28.71, 28.65, 28.02, 25.29, 22.09, 17.18, 13.89.

H3C11Xyl

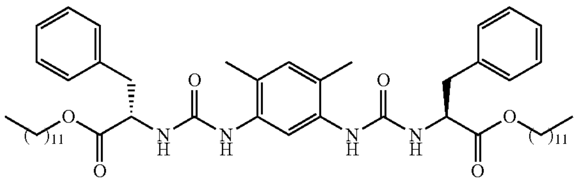

Preparation was achieved following the method B using dodecyl (S)-phenylalaninate ammonium tosylate salt and 4,6-dimethyl-1,3-diaminobenzene. The product is recrystallized twice in acetonitrile. 1.49 g (62%) of a pure product were obtained as a white paste.

$^1$H NMR (300 MHz, DMSO-$d_6$/THF-$d_8$ 2/1) δ 7.95 (s, 1H, ArH), 7.75 (s, 2H, NH), 7.36-7.15 (m, 10H, ArH and NH), 6.85 (s, 1H, ArH), 6.70 (d, 2H, ArH, $^2$J=7.6 Hz), 4.49 (q, 2H, NH—CH, $^2$J=6.7 Hz), 4.00 (t, 4H, COO—CH2, $^2$J=6.2 Hz), 3.08-2.91 (m, NH3-CH—CH2, 4H)), 2.05 (s, 6H, Ar—CH3), 1.50 (q, 4H, COOCHC2CH2, $^2$J=6.0 Hz), 1.30-1.15 (m, 36H, CH2), 0.85 (t, 6H, COO—CH2, $^2$J=6.7 Hz). $^{13}$C NMR (101 MHz, DMSO-$d_6$/THF-$d_8$ 2/1) δ 173.59, 156.09, 138.36, 136.86, 132.38, 130.49, 129.43, 127.72, 123.84, 117.23, 65.74, 55.28, 39.42, 32.81, 30.56, 30.53, 30.51, 30.43, 30.24, 30.19, 29.52, 26.81, 25.65, 25.45, 25.25, 25.05, 23.56, 18.43, 14.99. HRMS (ESI, m/z) 877.5807 [M+Na]$^+$, 877.5814 calculated for $C_{52}H_{78}N_4O_6Na$.

H3C12Tol

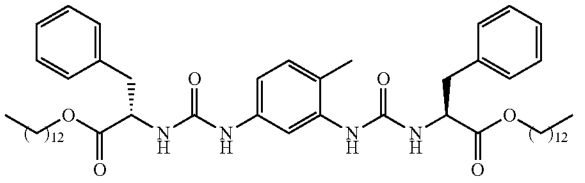

Preparation was achieved following the method A using tridecyl (S)-phenylalaninate ammonium tosylate salt. The product is recrystallized in acetonitrile. 757 mg (99%) of a pure product were obtained as a white paste.

$^1$H NMR (400 MHz, DMSO-$d_6$) δ 8.58 (s, 1H, ArH), 7.79 (s, 1H, NH), 7.73 (s, 1H, NH), 7.35-7.14 (m, 11H, ArH), 7.09 (d, 2H, ArH, J=7.6 Hz), 6.92 (d, 2H, NH, J=8.2 Hz), 6.26 (d, 1H, ArH, J=7.9 Hz), 4.56-4.43 (m, 2H, NH—CH), 4.00 (t, 4H, COO—CH2, J=6.5 Hz), 2.99 (q, 4H, NH3-

CH—CH2, J=7.3, 6.4 Hz), 2.07 (s, 3H, Ar—CH3), 1.58-1.41 (m, 4H, CH2), 1.36-1.07 (m, 36H, CH2), 0.85 (t, 6H, CH3, J=6.6 Hz). $^{13}$C NMR (101 MHz, DMSO-$d_6$) δ 172.16, 154.60, 138.09, 137.78, 136.84, 136.77, 129.90, 129.10, 128.22, 126.54, 119.37, 111.58, 109.95, 64.42, 53.96, 53.73, 37.69, 37.54, 31.29, 29.05, 29.02, 28.97, 28.89, 28.71, 28.64, 28.02, 25.28, 22.08, 17.18, 13.89. HRMS (ESI, m/z) 891.5964 $[M+Na]^+$, 891.5970 calculated for $C_{53}H_{80}N_4O_6Na$.

H3C13Tol

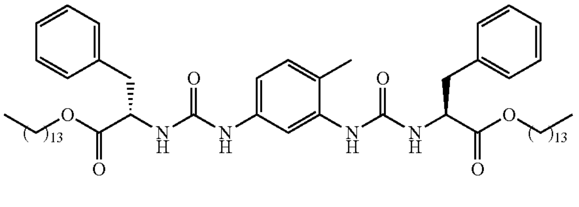

Preparation was achieved following the method A using tetradecyl (S)-phenylalaninate ammonium tosylate salt. The product is recrystallized in acetonitrile. 746 mg (96%) of a pure product were obtained as a white paste.

$^1$H NMR (400 MHz, DMSO-$d_6$/THF-d8 2/1) δ 8.60 (s, 1H, ArH), 7.79 (d, 2H, NH, J=16.7 Hz), 7.38-7.15 (m, 10H, ArH), 6.96 (d, 1H, ArH, J=7.8 Hz), 6.90 (d, 1H, ArH, J=8.3 Hz), 6.28 (d, 1H, NH, J=8.0 Hz), 4.57 (dd, 2H, NH—CH, J=14.9, 7.4 Hz), 4.03 (t, 4H, COO—CH2, J=6.7 Hz), 3.12-2.94 (m, 4H, NH3-CH—CH2), 2.11 (s, 3H, Ar—CH3), 1.64-1.46 (m, 4H, CH2), 1.43-1.06 (m, 40H, CH2), 0.87 (t, 6H, CH3, J=6.5 Hz). $^{13}$C NMR (101 MHz, DMSO-$d_6$/THF-d8 2/1) δ 172.11, 154.58, 154.45, 138.39, 137.97, 136.96, 136.90, 129.66, 129.10, 128.07, 126.37, 118.99, 114.60, 111.37, 109.69, 64.38, 53.94, 53.72, 38.04, 37.86, 31.43, 31.43, 29.19, 29.06, 28.85, 28.16, 25.44, 22.18, 22.18, 17.04, 13.59. HRMS (ESI, m/z) 919.6298 $[M+Na]^+$, 919.6283 calculated for $C_{55}H_{84}N_4O_6Na$.

H3C15Tol

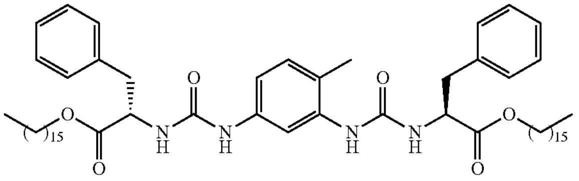

Preparation was achieved following the method A using hexadecyl (S)-phenylalaninate ammonium tosylate salt. The product is recrystallized in acetonitrile. 2.01 g (93%) of a pure product were obtained as a white paste.

$^1$H NMR (400 MHz, DMSO-$d_6$) δ 8.59 (s, 1H, NH), 7.81 (s, 1H, NH), 7.77 (d, 1H, ArH, J=2.2 Hz), 7.33-7.26 (m, 4H, ArH), 7.26-7.17 (m, 7H, ArH), 6.96 (d, 1H, ArH, J=7.8 Hz), 6.90 (d, 1H, NH, J=8.3 Hz), 6.27 (d, 1H, NH, J=7.9 Hz), 4.63-4.47 (m, 2H, NH—CH), 4.03 (t, 4H, COO—CH2, J=6.7 Hz), 3.11-2.94 (m, 4H, NH3-CH—CH2), 2.10 (s, 3H, Ar—CH3), 1.60-1.48 (m, 4H, CH2), 1.37-1.18 (m, 52H, CH2), 0.87 (t, 6H, CH3, J=6.7 Hz). $^{13}$C NMR (101 MHz, DMSO-$d_6$) δ 172.00, 154.48, 154.34, 138.25, 137.85, 136.84, 136.78, 129.57, 128.99, 127.98, 126.28, 118.93, 111.29, 109.62, 66.30, 66.08, 65.87, 65.65, 64.28, 53.84, 53.62, 37.90, 37.72, 31.31, 29.07, 29.03, 28.94, 28.73, 28.04, 25.32, 24.17, 23.97, 23.77, 22.07, 16.94, 13.51. HRMS (ESI, m/z) 835.5340 $[M+Na]^+$, 853.5344 calculated for $C_{49}H_{72}N_4O_6Na$.

H3C15Xyl

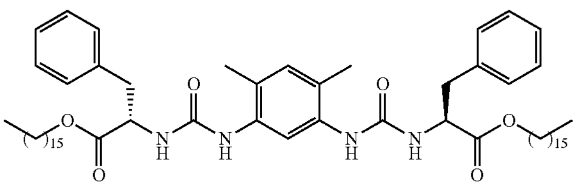

Preparation was achieved following the method B using hexadecyl (S)-phenylalaninate ammonium tosylate salt and 4,6-dimethyl-1,3-diaminobenzene. The product is recrystallized twice in acetonitrile. 1.05 g (64%) of a pure product were obtained as a white paste.

$^1$H NMR (400 MHz, DMSO-$d_6$/THF-d8 2/1) δ 8.02 (s, 1H, ArH), 7.77 (s, 2H, NH), 7.33-7.15 (m, 12H, ArH), 6.83 (s, 1H, ArH), 6.71 (d, 2H, NH, J=8.0 Hz), 4.57 (q, 2H, NH—CH, J=7.0 Hz), 4.02 (t, 4H, COO—CH2, J=6.5 Hz), 3.02 (dd, NH3-CH—CH2, 4H, J=6.6, 3.3 Hz), 2.08 (s, 6H, Ar—CH3), 1.60-1.45 (m, 4H, CH2), 1.39-1.13 (m, 62H, CH2), 0.87 (t, H, CH3, J=6.7 Hz). $^{13}$C NMR (101 MHz, DMSO-$d_6$/THF-d8 2/1) δ 172.11, 154.61, 136.88, 135.36, 130.90, 129.01, 127.95, 126.24, 122.33, 115.73, 64.25, 53.80, 31.31, 29.07, 29.03, 28.94, 28.73, 28.70, 28.03, 25.32, 22.07, 16.95, 13.51. HRMS (ESI, m/z) 989.7085 $[M+Na]^+$, 989.7066 calculated for $C_{60}H_{94}N_4O_6Na$.

H3C17Tol

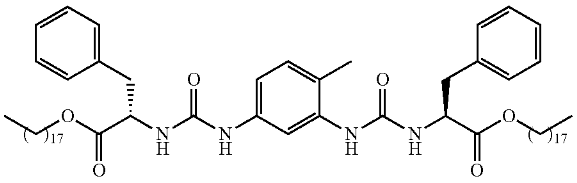

Preparation was achieved following the method A using octodecyl (S)-phenylalaninate ammonium tosylate salt. The product is recrystallized in acetonitrile. 923 mg (92%) of a pure product were obtained as a white paste. The S enantiomer was synthesized as well (88% yield).

$^1$H NMR (400 MHz, DMSO-$d_6$/THF-d8 2/1) δ 8.60 (s, 1H, NH), 7.82 (s, 1H, NH), 7.77 (d, 1H, ArH, J=2.2 Hz), 7.34-7.17 (m, 12H, ArH), 6.97 (d, 1H, NH, J=7.9 Hz), 6.90 (d, 1H, NH, J=8.3 Hz), 6.29 (d, 1H, ArH, J=8.0 Hz), 4.64-4.48 (m, 2H, NH—CH), 4.09-3.98 (m, 4H, COO—CH2), 3.12-2.95 (m, 4H, NH3-CH—CH2), 2.20-2.05 (m, 3H, Ar—CH3), 1.54 (p, 4H, CH2, J=6.5 Hz), 1.36-1.17 (m, 60H, CH2), 0.87 (t, 6H, CH3, J=6.7 Hz). $^{13}$C NMR (101 MHz, DMSO-$d_6$/THF-d8 2/1) δ 172.10, 154.59, 154.44, 138.40, 137.98, 136.97, 136.91, 129.64, 129.10, 128.05, 126.36, 118.98, 111.37, 109.70, 64.36, 53.95, 53.73, 38.05, 37.87, 31.44, 29.20, 29.16, 29.08, 28.86, 28.17, 25.46, 25.44, 22.19.

H3C7$d_5$-PheTol

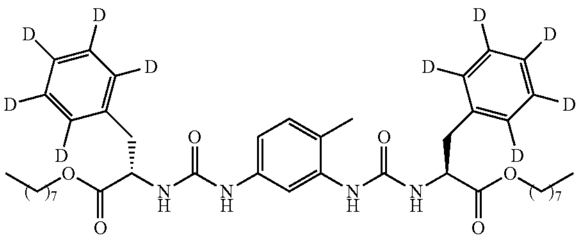

Preparation was achieved following the method A using octyl (S)-$d_5$-phenylalaninate ammonium tosylate salt. The product is recrystallized in acetonitrile. 649 mg (73%) of a pure product were obtained as a white paste.

$^1$H NMR (300 MHz, DMSO-$d_6$) δ 8.59 (s, 1H, NH), 7.80 (s, 1H, ArH), 7.72 (s, 1H, NH), 7.10 (d, 1H, NH, $^2$J=8.3 Hz), 6.93 (d, 2H, ArH, $^2$J=7.4 Hz), 6.27 (d, 1H, NH, $^2$J=8.1 Hz), 4.49 (qi, 2H, NH—CH, $^2$J=7.2 Hz), 4.01 (t, 4H, COO—CH2, $^2$J=6.5 Hz), 3.05-2.95 (m, 4H, COO—CH2-CH2), 2.07 (s, 3H, Ar—CH3), 1.56-1.44 (m, 4H, COO—CH2-CH2-CH2), 1.33-1.15 (m, 44H, CH2), 0.84 (t, 3H, CH3, $^2$J=6.5 Hz). $^{13}$C NMR (101 MHz, DMSO-$d_6$) δ 172.20, 154.62, 154.48, 138.10, 137.79, 136.66, 136.59, 129.93, 119.43, 111.61, 109.97, 64.45, 53.96, 53.74, 37.60, 37.44, 31.20, 28.60, 28.55, 28.02, 25.28, 22.06, 17.18, 13.89. HRMS (ESI, m/z) 761.5039 [M+Na]$^+$, 761.5033 calculated for $C_{35}H_{50}D_{10}N_4O_6Na$.

3.2. Halogen Functionalized Ester Bis-Ureas

Br3C11Tol

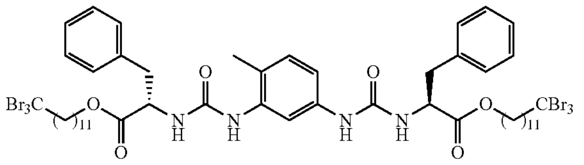

Preparation was achieved following the method A using 12-tribromododecyl (S)-phenylalaninate ammonium tosylate salt. The product is recrystallized in acetonitrile. 2.04 g (84%) of a pure product were obtained as a white paste.

$^1$H NMR (300 MHz, DMSO-$d_6$) δ 8.59 (s, 1H, NH), 7.80 (s, 1H, NH), 7.72 (d, 1H, ArH, $^2$J=1.7 Hz), 7.36-7.02 (m, 11H, ArH and NH), 6.93 (d, 2H, ArH, $^2$J=8.2 Hz), 6.27 (d, 2H, ArH, $^2$J=7.7 Hz), 4.48 (p, 2H, NH—CH, $^2$J=7.0 Hz), 4.01 (t, 4H, COO—CH2, $^2$J=6.3 Hz), 3.06-2.90 (m, 8H, NH3-CH—CH2 and CBr3-CH2), 2.07 (s, 3H, Ar—CH3), 1.67 (p, 4H, COO—CH2-CH2, $^2$J=7.5 Hz), 1.59-1.45 (m, 4H, ArO—CH2-CH2), 1.45-1.15 (m, 28H, CH2). $^{13}$C NMR (101 MHz, DMSO-$d_6$) δ 172.17, 154.60, 138.08, 137.78, 136.84, 136.77, 129.93, 129.12, 128.25, 126.57, 119.38, 111.58, 109.92, 64.45, 58.68, 53.72, 43.37, 37.69, 37.54, 29.16, 28.86, 28.74, 28.62, 28.02, 27.08, 25.27, 17.22. HRMS (ESI, m/z) 1335.0275 [M+Na]$^+$, 1335.0247 calculated for $C_{51}H_{70}Br_6N_4O_6Na$.

Br3C11Xyl

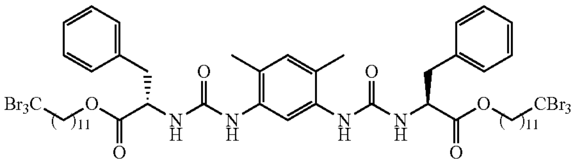

Preparation was achieved following the method B using 12-tribromododecyl (S)-phenylalaninate ammonium tosylate salt and 4,6-dimethyl-1,3-diaminobenzene. The product is recrystallized in acetonitrile. 707 mg (28%) of a pure product were obtained as a white paste.

$^1$H NMR (300 MHz, DMSO-$d_6$) δ 7.95 (s, 1H, ArH), 7.75 (s, 2H, NH), 7.35-7.15 (m, 13H, ArH and NH), 6.98-6.80 (m, 8H, ArH and NH), 6.85 (s, 1H, ArH), 6.70 (d, 2H, ArH, $^2$J=7.8 Hz), 4.49 (q, 2H, NH—CH, $^2$J=7.2 Hz), 4.00 (t, 4H, COO—CH2, $^2$J=6.4 Hz), 3.05-2.90 (m, CBr3-CH2 and NH3-CH—CH2, 8H), 2.05 (s, 6H, Ar—CH3), 1.67 (p, 4H, COO—CH2-CH2, $^2$J=7.3 Hz), 1.58-1.15 (m, 32H, CH2). $^{13}$C NMR (101 MHz, DMSO-$d_6$) δ 172.26, 154.71, 144.47, 137.61, 136.86, 135.25, 131.18, 129.11, 128.22, 126.53, 122.38, 64.42, 58.65, 53.90, 43.37, 37.72, 29.15, 28.83, 28.71, 28.60, 28.00, 27.06, 25.25, 17.18. HRMS (ESI, m/z) 1349.0413 [M+Na]$^+$, 1349.0403 calculated for $C_{52}H_{72}Br_6N_4O_6Na$.

Br3C11Cl

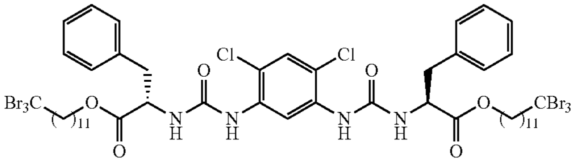

Preparation was achieved following the method B using 12-tribromododecyl (S)-phenylalaninate ammonium tosylate salt and 4,6-dichloro-1,3-diaminobenzene. The product is recrystallized in acetonitrile. 1.09 g (68%) of pure product were obtained as a white powder.

$^1$H NMR (300 MHz, DMSO-$d_6$) δ 8.91 (s, 1H, ArH), 8.19 (s, 2H, NH), 7.50-7.12 (m, 13H, ArH and NH), 4.57-4.42 (m, 2H, NH—CH), 4.00 (t, 4H, COO—CH2, $^2$J=4.7 Hz), 2.97 (m, NH3-CH—CH2 and CBr3-CH2, 8H), 1.78-1.58 (m, 4H, COO—CH2-CH2), 1.65-1.10 (m, 32H, CH2). $^{13}$C NMR (101 MHz, DMSO-$d_6$) δ 171.97, 153.86, 136.72, 135.42, 129.05, 128.26, 128.13, 126.59, 114.30, 112.77, 64.50, 58.67, 53.98, 43.36, 37.48, 29.15, 28.85, 28.73, 28.61, 27.99, 27.08, 25.27. HRMS (ESI, m/z) 1388.9324 [M+Na]$^+$, 1388.9311 calculated for $C_{50}H_{66}Br_6Cl_2N_4O_6Na$.

C13C11Xyl

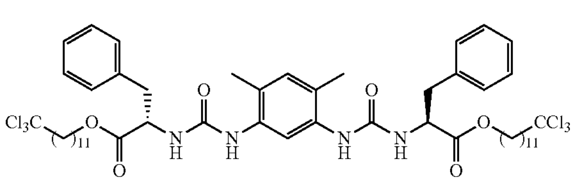

Preparation was achieved following the method B using 12-trichlorododecyl (S)-phenylalaninate ammonium tosylate salt and 4,6-dimethyl-1,3-diaminobenzene. The product is recrystallized in acetonitrile. 291 mg (64%) of a pure product were obtained as a white paste.

$^1$H NMR (300 MHz, DMSO-$d_6$) δ 7.95 (s, 1H, ArH), 7.75 (s, 2H, NH), 7.35-7.15 (m, 15H, ArH and NH), 6.98-6.80 (m, 8H, ArH and NH), 6.85 (s, 1H, ArH), 6.70 (d, 2H, ArH, $^2$J=7.8 Hz), 4.49 (q, 2H, NH—CH, $^2$J=7.2 Hz), 4.00 (t, 4H, COO—CH2, $^2$J=6.4 Hz), 3.04-2.94 (m, NH3-CH—CH2, 4H), 2.72 (t, CC13-CH2, $^2$J=7.9 Hz), 2.05 (s, 6H, Ar—CH3), 1.67 (p, 4H, COO—CH2-CH2, $^2$J=7.3 Hz), 1.58-1.15 (m, 32H, CH2). $^{13}$C NMR (75 MHz, DMSO-$d_6$) δ 172.76, 155.22, 137.37, 135.77, 131.69, 129.61, 128.72, 127.02, 122.89, 116.16, 101.03, 64.92, 54.62, 54.41, 38.25, 29.34, 29.31, 29.17, 29.11, 28.51, 27.98, 26.59, 25.77, 17.68. HRMS (ESI, m/z) 1083.3474 [M+Na]$^+$, 1083.3446 calculated for $C_{52}H_{72}Cl_6N_4O_6Na$.

Part 2: Physico-Rheological Tests

Example 4

Effect of Temperature on Relative Viscosity

The aim of this experiment was to measure the effect of the temperature on the evolution of the relative viscosity of non-polar liquids.

Viscosity is a measure of a fluid's resistance to flow. In this experiment, the relative viscosity has been evaluated by measuring the flow time of the sample at various temperatures using 0.1 mM solution of H3C11Xyl either in methylcyclohexane or in dodecane.

Figure 2:
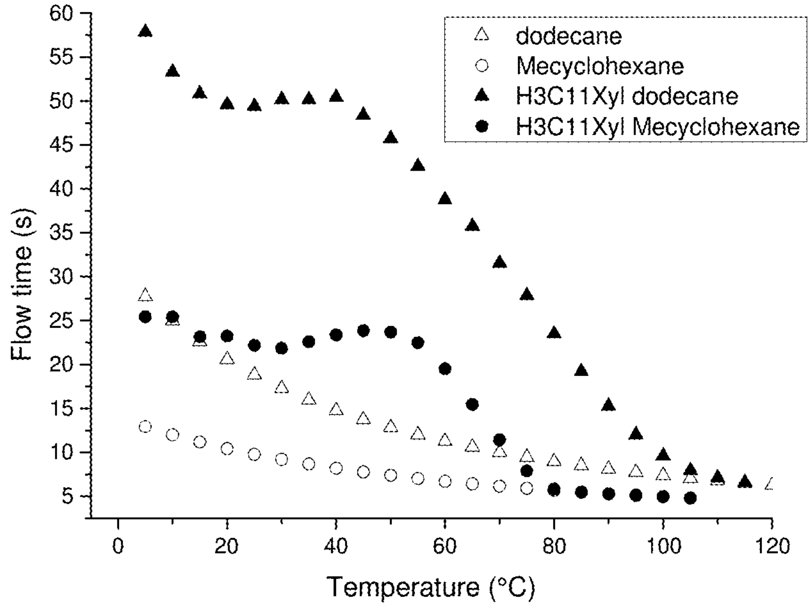
FIG. 2 is a graph showing the evolution of flow time in function of the temperature for dodecane and methylcyclohexane and corresponding solutions comprising H3C11Xyl.

The results (FIG. 2) show that:

for the liquids only—i.e. free of H3C11Xyl—(dodecane or methylcyclohexane), the flow time dramatically decreases when the temperature increases until 120° C.;

when H3C11Xyl is added to either dodecane or methylcyclohexane (non-polar liquid), the flow time is higher than the one of the corresponding solution without the compound of invention;

in the temperature range from about 20° C. to 45° C. for the solution of H3C11Xyl in dodecane or in the range from about 22° C. to 55° C. for the solution of H3C11Xyl in methylcyclohexane, the flow time of solutions comprising H3C11Xyl does not decrease, and even slightly increases, when the temperature rises.

In conclusion, these experiments evidence that the compound of the invention (ester bis-ureas) acts as a thermo-thickening agent when added in a non-polar liquid such as dodecane or methylcycloxane.

Example 5

Influence of Alkyl Chain Length

The aim of this experiment is to investigate the influence of the length of the alkyl chain on the evolution of the relative viscosity by comparing an ester bis-urea with an octyl chain, a dodecyl chain and a hexadecyl chain.

This experiment is carried out by solubilizing in a non-polar liquid at a concentration of 0.1 mM: H3C7Xyl (ester bis-urea with octyl chain), H3C11Xyl (ester bis-urea with dodecyl chain) or H3C15Xyl (ester bis-urea with hexadecyl chain), as described above. The non-polar liquids are chosen among methylcyclohexane and dodecane.

Figure 3:
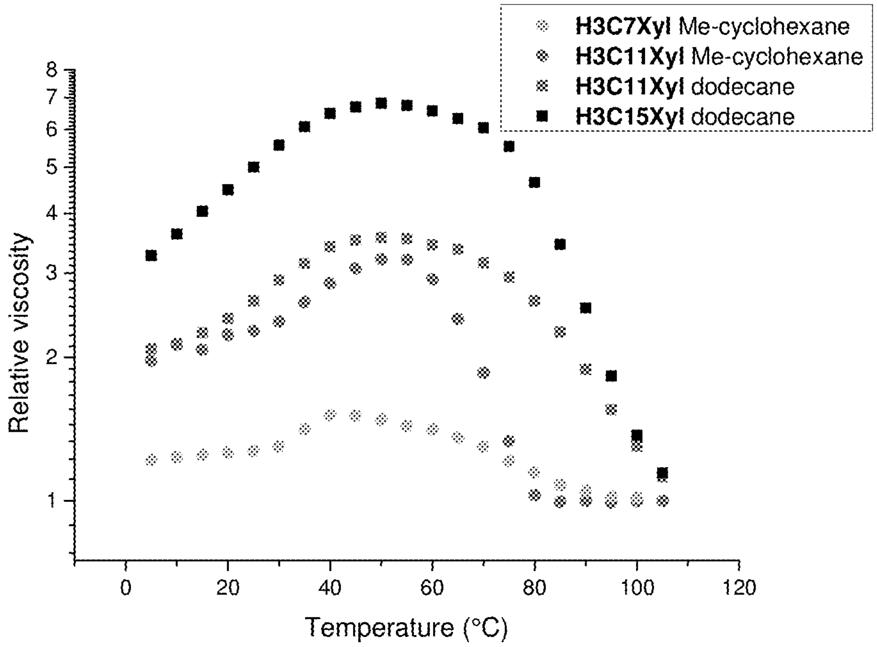
FIG. 3 is a graph showing the relative viscosity in function of the temperature for dodecane or methylcyclohexane solutions comprising H3C7Xyl, H3C11Xyl or H3C15Xyl.

The results (FIG. 3) show that for all solutions comprising an ester bis-ureas with octyl (H3C7Xyl), dodecyl (H3C11Xyl) or hexadecyl (H3C15Xyl) chain, the relative viscosity increases or is maintained when solutions are heated from 5° C. to about 70° C.

In conclusion, these experiments evidence that ester bis-ureas with long alkyl chains act as efficient thermo-thickening agent when added in a non-polar liquid heated at a temperature ranging from about 5° C. to 70° C.

Example 6

Rheology Test

The aim of this experiment is to show the rheology behavior of a composition of the invention.

For this purpose, the storage modulus (G'—elastic response) and the loss modulus (G"—viscous behavior) have been measured at 1 rad/s, for a solution of H3C11Xyl in dodecane (4.1 g/L). G' and G" allow having information regarding the complex viscosity of a sample.

Figure 4:
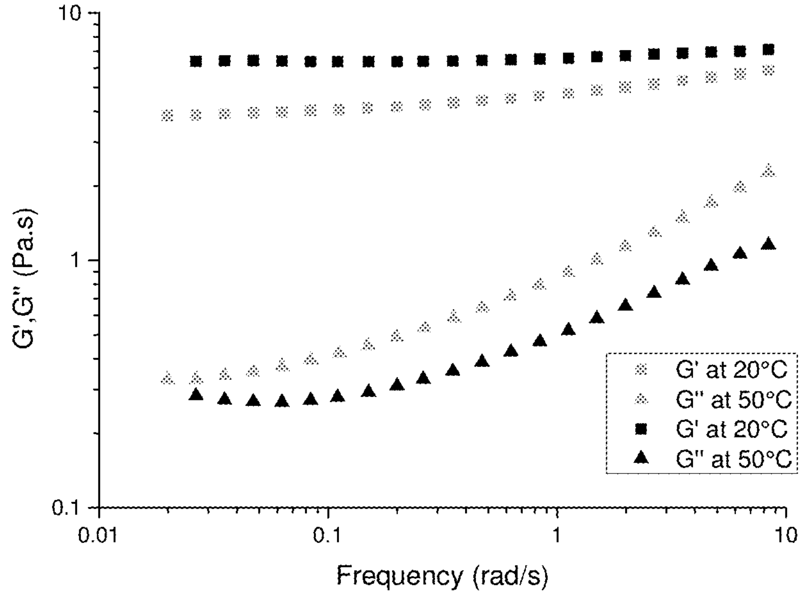
FIG. 4 is a graph showing the evolution of G' and G" modulus for a solution of H3C11Xyl in dodecane (4.1 g/L) in function of frequency (rad/s).
Figure 5:
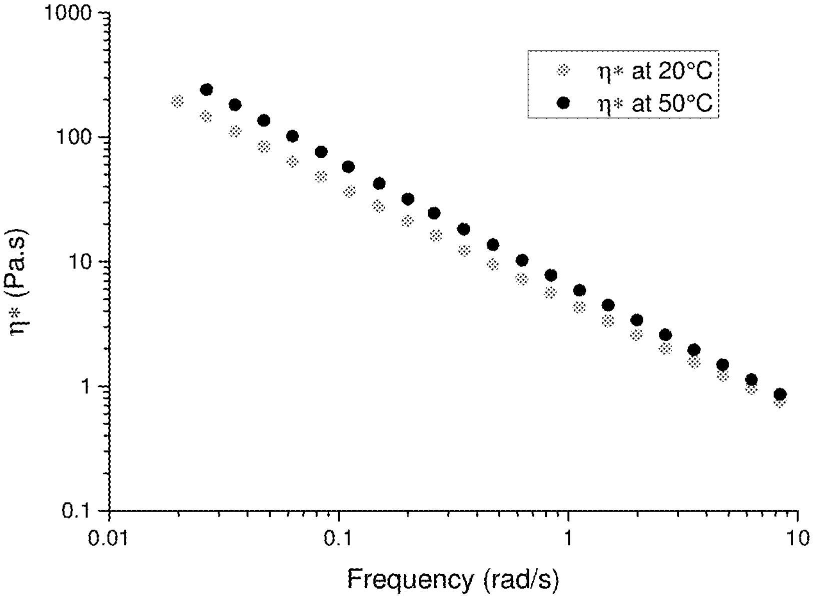
FIG. 5 is a graph showing the evolution of complex viscosity for a solution of H3C11Xyl in dodecane (4.1 g/L) in function of frequency (rad/s).

The results (FIGS. 4 and 5) show that the complex viscosity increases by 1.5 for a solution comprising a compound of the invention heated at a temperature ranging from 20° C. to 50° C.

The invention claimed is:

1. A method for thermo-thickening a composition comprising the addition to said composition of a compound of general formula (IV bis):

(IVbis)

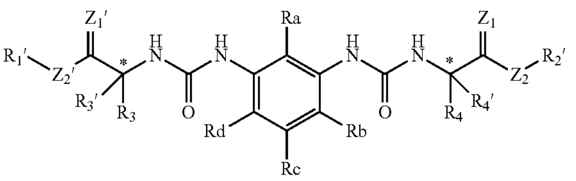

wherein:

$R_a$, $R_b$, $R_c$ and $R_d$ are each independently selected from H, alkyl, heteroalkyl, alkoxy, amino, alkylamino and halo;

$R_1'$ and $R_2'$ are each independently selected from linear alkyl, heteroalkyl, alkenyl, heteroalkenyl, alkynyl, heteroalkynyl and macromolecular groups, substituted or not substituted by one or more halo;

$R_3$, $R_3$, $R_4$, and $R_4'$ are each independently selected from H, alkyl, alkenyl, aryl, heteroalkyl, heteroalkenyl, heteroaryl, alkylaryl, arylalkyl, heteroarylalkyl or alkylheteroaryl, substituted or not substituted by guanidine, aryl, pyrrolidine, imidazole, hydroxyaryl, carboxy, selanyl, hydroxyl, amide, thiol, alkylthio, amino, deuterium or halo;

$Z_1$, $Z_1'$, $Z_2$, and $Z_2'$ represent O atoms; and optionally, * stands for a stereogenic center;

provided that $R_1'$ and $R_2'$ do not represent both a methyl group.

2. The method according to claim 1, wherein in the compound of formula (IVbis), $R_a$ and $R_c$ are both H.

3. The method according to claim 1, wherein said composition is a non-polar liquid.

4. The method according to claim 1, wherein thermo-thickening is performed at a temperature ranging from 5° C. to 100° C.

5. The method according to claim 1, for further improving the cold flow property of a non-polar liquid.

6. A compound of general formula (IV bis):

(IVbis)

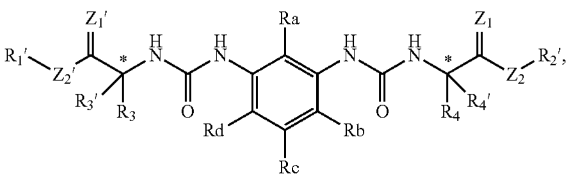

wherein:

$R_a$, $R_b$, $R_c$ and $R_d$ are each independently selected from H, alkyl, heteroalkyl, alkoxy, amino, alkylamino and halo;

$R_1$' and $R_2$' are each independently selected from linear alkyl, heteroalkyl, alkenyl, heteroalkenyl, alkynyl, heteroalkynyl and macromolecular groups, substituted or not substituted by one or more halo;

$R_3$', $R_3$, $R_4$ and $R_4$' are each independently selected from H, alkyl, alkenyl, aryl, heteroalkyl, heteroalkenyl, heteroaryl, alkylaryl, arylalkyl, heteroarylalkyl or alkylheteroaryl, substituted or not substituted by guanidine, aryl, pyrrolidine, imidazole, hydroxyaryl, carboxy, selanyl, hydroxyl, amide, thiol, alkylthio, amino, deuterium or halo;

$Z_1$, $Z_1$', $Z_2$ and $Z_2$' represent O atoms; and optionally, * stands for a stereogenic center.

7. The compound according to claim 6, selected from:

(2S,2'S)-dihexyl 2,2'-((((4-methyl-1,3-phenylene)bis(azanediyl))bis(carbonyl))bis(azanediyl))bis(3-phenylpropanoate);

(2S,2'S)-diheptyl 2,2'-((((4-methyl-1,3-phenylene)bis(azanediyl))bis(carbonyl))bis(azanediyl))bis(3-phenylpropanoate);

(2S,2'S)-dioctyl 2,2'-((((4-methyl-1,3-phenylene)bis(azanediyl))bis(carbonyl))bis(azanediyl))bis(3-phenylpropanoate);

(2S,2'S)-dioctyl 2,2'-((((4,6-dimethyl-1,3-phenylene)bis(azanediyl))bis(carbonyl))bis(azanediyl))bis(3-phenylpropanoate);

(2S,2'S)-dioctyl 2,2'-((((4,6-dichloro-1,3-phenylene)bis(azanediyl))bis(carbonyl))bis(azanediyl))bis(3-phenylpropanoate);

(2S,2'S)-dinonyl 2,2'-((((4-methyl-1,3-phenylene)bis(azanediyl))bis(carbonyl))bis(azanediyl))bis(3-phenylpropanoate);

(2 S,2'S)-dinonyl 2,2'-((((4,6-dimethyl-1,3-phenylene)bis(azanediyl))bis(carbonyl))bis(azanediyl))bis(3-phenylpropanoate);

(2 S,2'S)-didecyl 2,2'-((((4-methyl-1,3-phenylene)bis(azanediyl))bis(carbonyl))bis(azanediyl))bis(3-phenylpropanoate);

(2 S,2'S)-diundecyl 2,2'-((((4-methyl-1,3-phenylene)bis(azanediyl))bis(carbonyl))bis(azanediyl))bis(3-phenylpropanoate);

(2 S,2'S)-didodecyl 2,2'-((((4-methyl-1,3-phenylene)bis(azanediyl))bis(carbonyl))bis(azanediyl))bis(3-phenylpropanoate);

(2 S,2'S)-didodecyl 2,2'-((((4,6-dimethyl-1,3-phenylene)bis(azanediyl))bis(carbonyl))bis(azanediyl))bis(3-phenylpropanoate);

(2 S,2'S)-ditridecyl 2,2'-((((4-methyl-1,3-phenylene)bis(azanediyl))bis(carbonyl))bis(azanediyl))bis(3-phenylpropanoate);

(2S,2'S)-ditetradecyl 2,2'-((((4-methyl-1,3-phenylene)bis(azanediyl))bis(carbonyl))bis(azanediyl))bis(3-phenylpropanoate);

(2 S,2'S)-dihexadecyl 2,2'-((((4-methyl-1,3-phenylene)bis(azanediyl))bis(carbonyl))bis(azanediyl))bis(3-phenylpropanoate);

(2 S,2'S)-dihexadecyl 2,2'-((((4,6-dimethyl-1,3-phenylene)bis(azanediyl))bis(carbonyl))bis(azanediyl))bis(3-phenylpropanoate);

(2 S,2'S)-dioctadecyl 2,2'-((((4-methyl-1,3-phenylene)bis(azanediyl))bis(carbonyl))bis(azanediyl))bis(3-phenylpropanoate);

(2 S,2'S)-dioctyl 2,2'-((((4-methyl-1,3-phenylene)bis(azanediyl))bis(carbonyl))bis(azanediyl))bis(3-pentadeuteriumphenylpropanoate);

(2S,2'S)-bis(12,12,12-tribromododecyl) 2,2'-((((4-methyl-1,3-phenylene)bis(azanediyl))bis(carbonyl))bis(azanediyl))bis(3-phenylpropanoate);

(2S,2'S)-bis(12,12,12-tribromododecyl) 2,2'-((((4,6-dimethyl-1,3-phenylene)bis(azanediyl))bis(carbonyl))bis(azanediyl))bis(3-phenylpropanoate);

(2S,2'S)-bis(12,12,12-tribromododecyl) 2,2'-((((4,6-dichloro-1,3-phenylene)bis(azanediyl))bis(carbonyl))bis(azanediyl))bis(3-phenylpropanoate); and (2S,2'S)-bis(12,12,12-trichlorododecyl) 2,2'-((((4,6-dimethyl-1,3-phenylene)bis(azanediyl))bis(carbonyl))bis(azanediyl))bis(3-phenylpropanoate).

8. A composition comprising at least one compound of claim 6, and a non-polar liquid.

9. The composition according to claim 8, wherein the non-polar liquid is selected from an oil (or lubricant), a monomer, a thermosetting resin, a perfume or a fuel.

10. The composition according to claim 8, wherein the compound is at a concentration ranging from more than 0 to 5% by weight to the total weight of the composition.

11. A process for manufacturing a compound of formula (IV bis):

(IVbis)

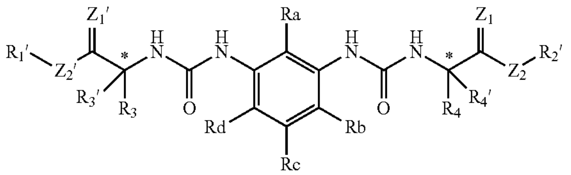

wherein:

$R_a$, $R_b$, $R_c$ and $R_d$ are each independently selected from H, alkyl, heteroalkyl, alkoxy, amino, alkylamino and halo;

$R_1$' and $R_2$' are each independently selected from linear alkyl, heteroalkyl, alkenyl, heteroalkenyl, alkynyl, heteroalkynyl and macromolecular groups, substituted or not substituted by one or more halo;

$R_3$', $R_3$, $R_4$, and $R_4$' are each independently selected from H, alkyl, alkenyl, aryl, heteroalkyl, heteroalkenyl, heteroaryl, alkylaryl, arylalkyl, heteroarylalkyl or alkylheteroaryl, substituted or not substituted by guanidine, aryl, pyrrolidine, imidazole, hydroxyaryl, carboxy, selanyl, hydroxyl, amide, thiol, alkylthio, amino, deuterium or halo;

$Z_1$, $Z_1$', $Z_2$ and $Z_2$' represent O atoms; and optionally, * stands for a stereogenic center;

said process comprising reacting at least one ester ammonium salt of formula (A-1):

(A-1)

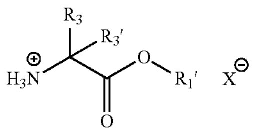

wherein $R_3$' and $R_3$ are each independently selected from H, alkyl, alkenyl, aryl, heteroalkyl, heteroalkenyl, heteroaryl, alkylaryl, arylalkyl, heteroarylalkyl or alkylheteroaryl, substituted or not substituted by guanidine, aryl, pyrrolidine, imidazole, hydroxyaryl, carboxy, selanyl, hydroxyl, amide, thiol, alkylthio, amino, deuterium or halo;

$R_1$' is each independently selected from linear alkyl, heteroalkyl, alkenyl, heteroalkenyl, alkynyl and heteroalkynyl group, substituted or not substituted by one or more halo; and $X^-$ is an anion with (a) either a diisocyanate of general formula (A-2bis):

(A-2bis)

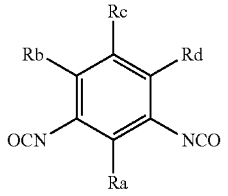

wherein $R_a$, $R_b$, $R_c$ and $R_d$ are each independently selected from H, alkyl, heteroalkyl, alkoxy, amino, alkylamino and halo;

(b) or a mixture of reagents allowing the in situ preparation of diisocyanate of formula (A-2bis).

12. The process according to claim 11, further comprising a preliminary step of preparing ester ammonium salt of formula (A-1) by reacting an amino acid and an alcohol.

13. The method according to claim 1, wherein said composition is selected from an oil, a grease, a monomer, a thermosetting resin, a perfume or a fuel.

14. The method according to claim 1, wherein $R_b$ and $R_d$ are each independently selected from H, $C_1$-$C_4$ alkyl, $C_1$-$C_4$ heteroalkyl, $C_1$-$C_4$ alkoxy, $C_1$-$C_4$ dialkylamino and halo.

15. The method according to claim 1, wherein $R_1$' and $R_2$' are each independently selected from linear alkyl or linear heteroalkyl group, said linear group being substituted or not substituted by one or more halo.

16. The method according to claim 1, wherein $R_3$', $R_3$, $R_4$, $R_4$' $R_5$, $R_5$', $R_6$ and $R_6$' are each independently selected from H, $C_1$-$C_{12}$ alkyl substituted by at least one aryl, said aryl being substituted or not substituted by one or more halo or deuterium.

* * * * *